US006299588B1

(12) United States Patent
Fratrick

(10) Patent No.: US 6,299,588 B1
(45) Date of Patent: *Oct. 9, 2001

(54) QUICK RELEASE MECHANISM FOR ORTHOPEDIC LIMB BRACE

(76) Inventor: Richard A. Fratrick, 737 W. Glendale Ave., Glendale, WI (US) 53209

( * ) Notice: Subject to any disclaimer, the term of this patent is extended or adjusted under 35 U.S.C. 154(b) by 0 days.

This patent is subject to a terminal disclaimer.

(21) Appl. No.: 09/211,652

(22) Filed: Dec. 15, 1998

Related U.S. Application Data

(63) Continuation-in-part of application No. 08/503,197, filed on Jul. 17, 1995, now Pat. No. 5,851,194.

(51) Int. Cl.⁷ .............................. A61F 5/00; A44B 17/00
(52) U.S. Cl. .................... 602/27; 602/28; 24/625
(58) Field of Search ...................... 602/5, 16, 23, 602/27–29; 24/625, 638, 684; 623/13, 27, 28, 31, 32, 38, 43, 47

(56) References Cited

U.S. PATENT DOCUMENTS

| 1,737,246 | * | 11/1929 | Jones ............................ 234/625 X |
| 3,064,644 | * | 11/1962 | Patterson ............................ 602/23 |
| 4,564,365 | * | 1/1986 | Winer et al. ...................... 623/38 X |
| 4,672,725 | * | 6/1987 | Kasai .................................. 24/625 |
| 4,712,280 | * | 12/1987 | Fildan ................................ 24/625 |
| 4,825,515 | * | 5/1989 | Wolterstorff ....................... 24/625 |
| 4,831,694 | * | 5/1989 | Kong .................................. 24/625 |
| 5,078,128 | * | 1/1992 | Grim et al. ......................... 602/23 |
| 5,116,382 | * | 5/1992 | Steinkamp et al. ................. 623/38 |
| 5,144,725 | * | 9/1992 | Krauss .............................. 24/625 |
| 5,222,279 | * | 6/1993 | Franco et al. ..................... 24/625 |
| 5,250,021 | * | 10/1993 | Chang ................................ 602/27 |
| 5,291,641 | * | 3/1994 | Morino .............................. 24/625 |
| 5,311,649 | * | 5/1994 | Suh .................................... 24/625 |
| 5,322,037 | * | 6/1994 | Tozawa .......................... 24/625 X |
| 5,355,562 | * | 10/1994 | Matoba et al. .................... 24/625 |
| 5,368,551 | * | 11/1994 | Zukerman ...................... 602/27 X |
| 5,419,020 | * | 5/1995 | Murai ................................. 24/625 |
| 5,429,588 | * | 7/1995 | Young et al. ...................... 602/27 |
| 5,443,039 | * | 8/1995 | Suchowski ..................... 24/625 X |
| 5,443,471 | * | 8/1995 | Swajger ......................... 623/13 X |
| 5,466,472 | * | 11/1995 | Matoba .............................. 24/625 |
| 5,507,076 | * | 4/1996 | Anscher ............................ 24/625 |
| 5,507,837 | * | 4/1996 | Laghi ................................. 623/38 |
| 5,546,642 | * | 8/1996 | Anscher ............................ 24/625 |
| 5,851,194 | * | 12/1998 | Fratrick ............................. 602/28 |

FOREIGN PATENT DOCUMENTS

155917 * 12/1920 (GB) ................................... 623/38

* cited by examiner

Primary Examiner—Denise Pothier
(74) Attorney, Agent, or Firm—Patula & Associates, P.C.

(57) ABSTRACT

A quick release orthopedic limb brace having an upright assembly and a clip member. The clip member is quickly and selectively inserted and removed from a clip housing on the upright assembly, at the convenience of a user. When the clip is locked in the clip housing, the resulting joint connection effectively prevents relative movement between the clip and the upright assembly to prevent injury or harm to a user. In an alternate embodiment, the upright remains pivotal.

40 Claims, 20 Drawing Sheets

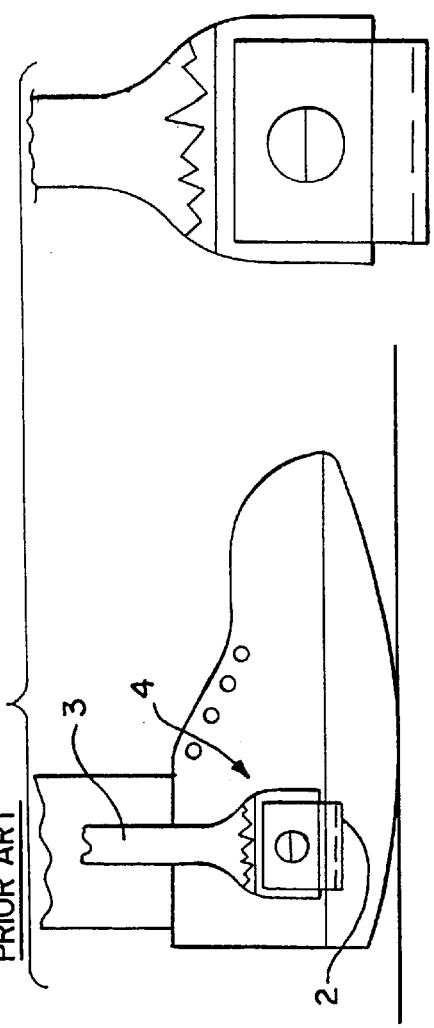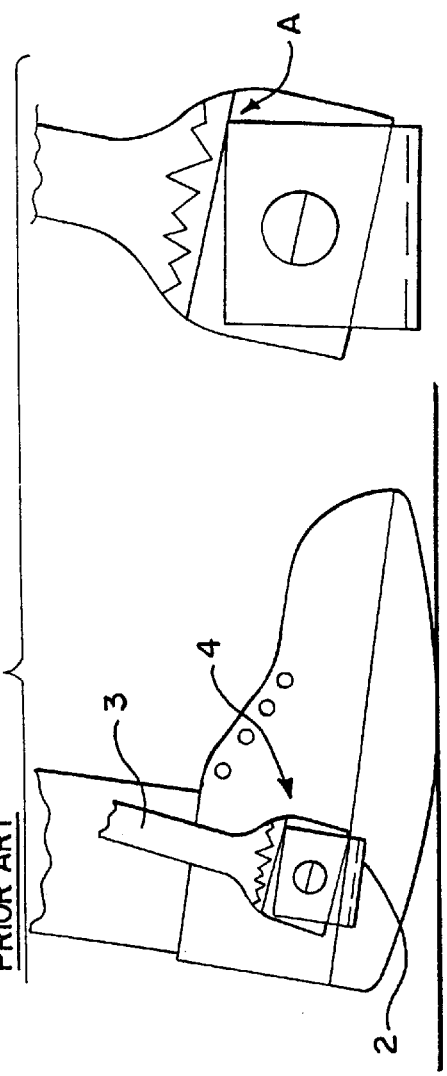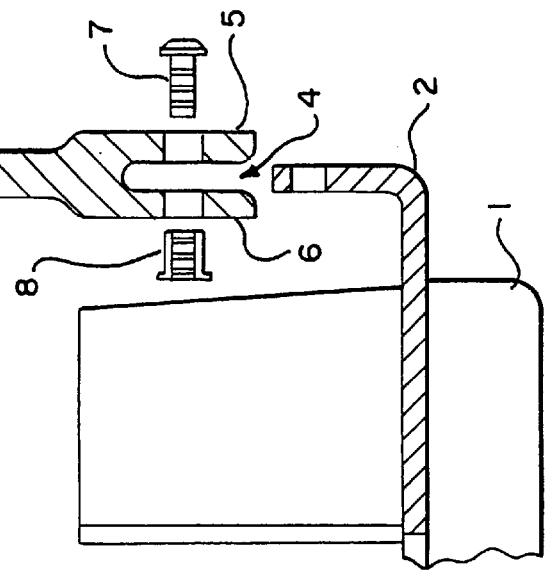

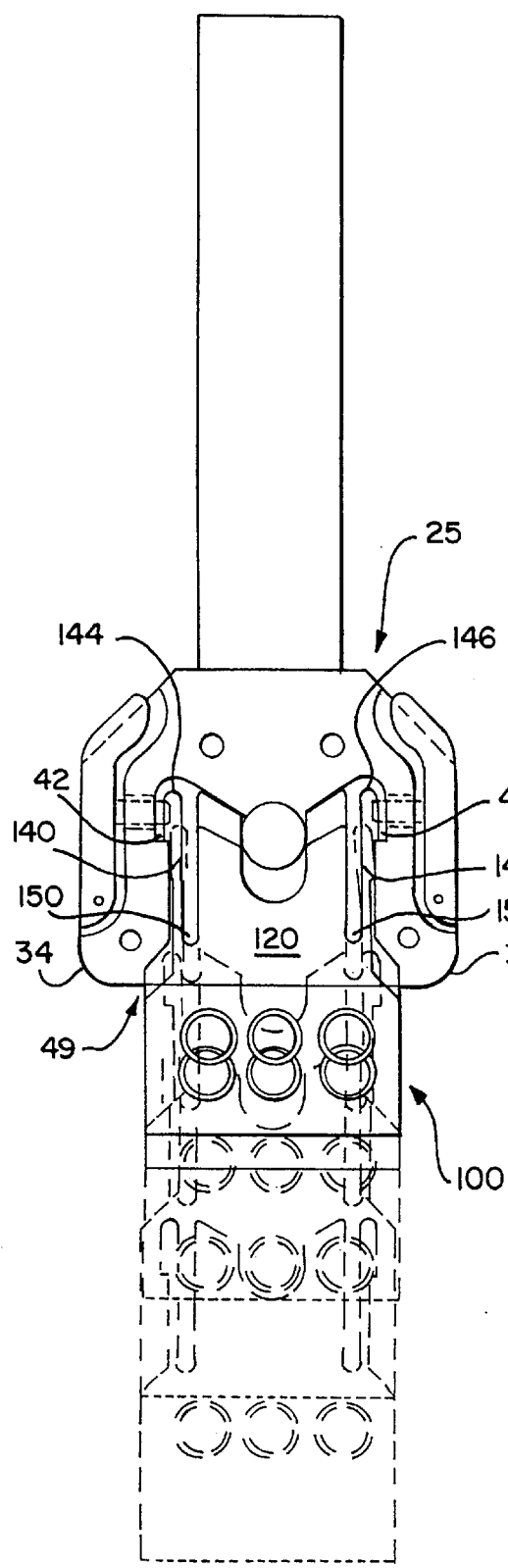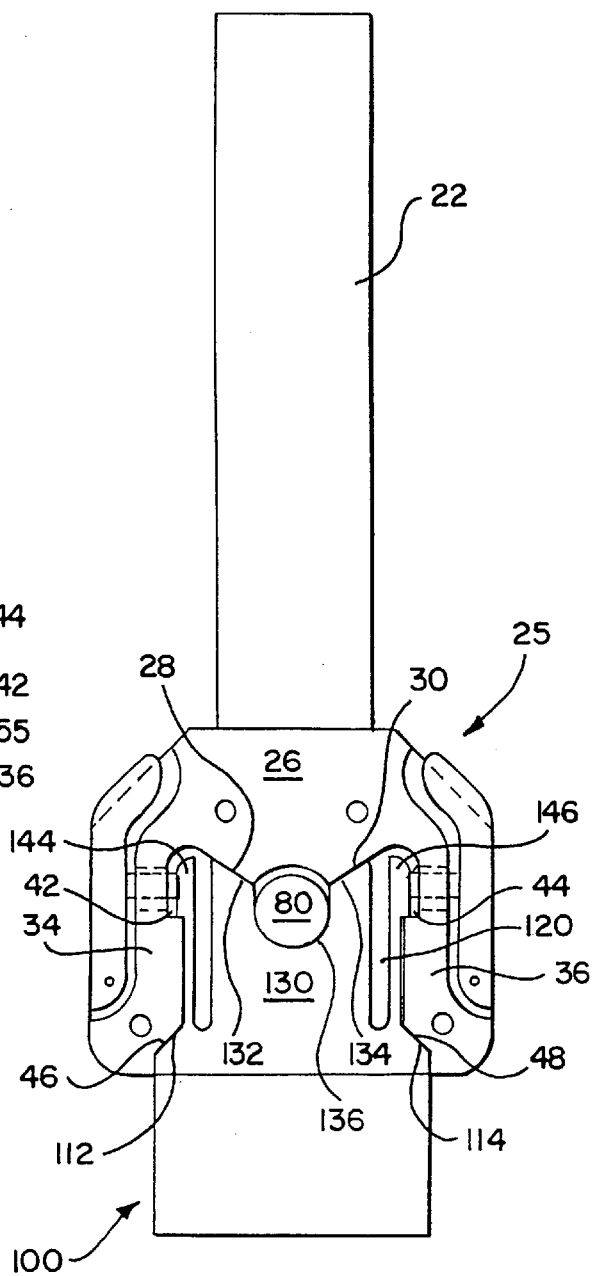

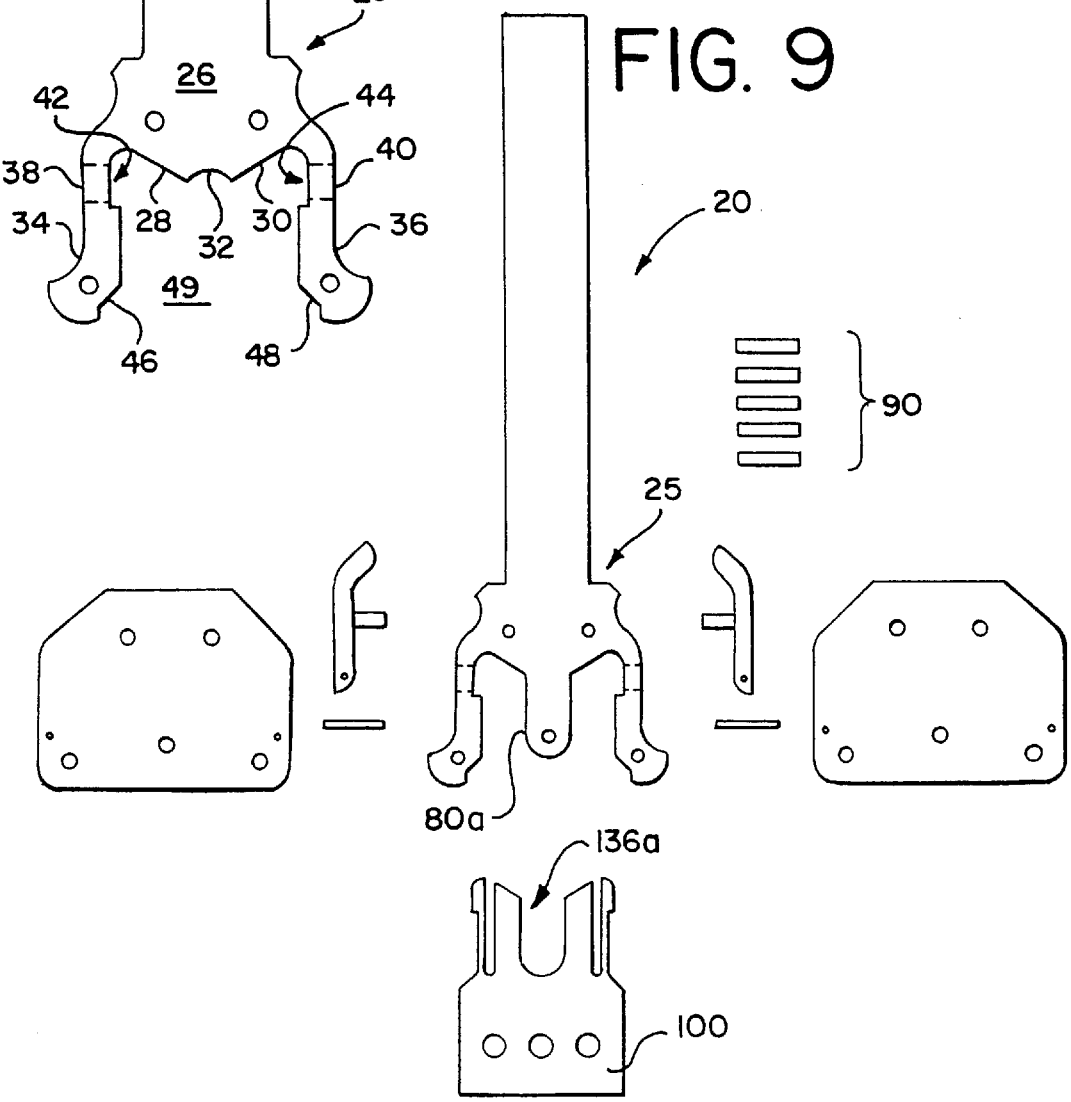

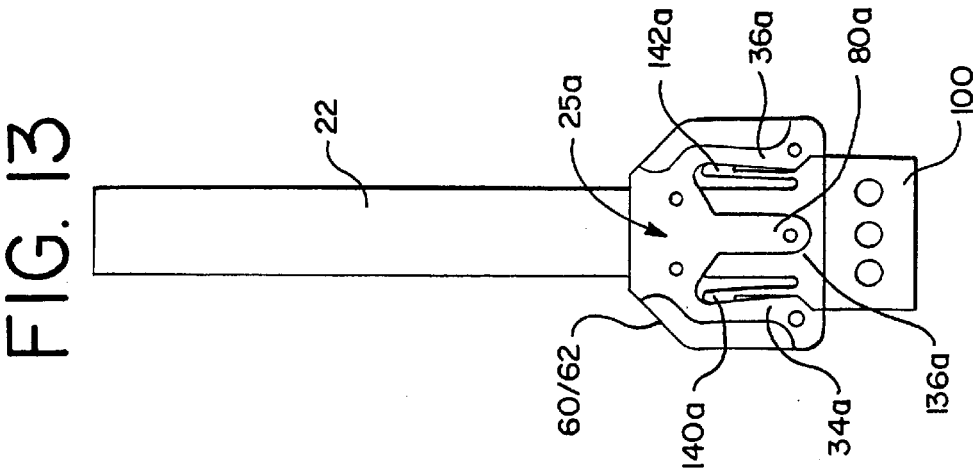
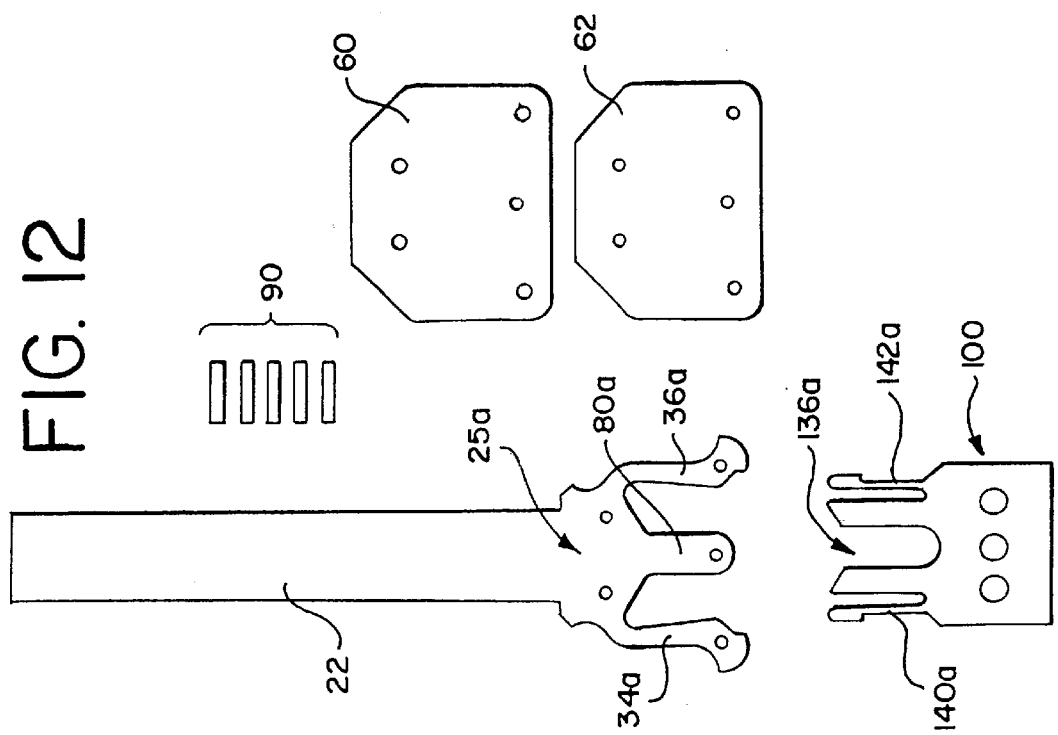

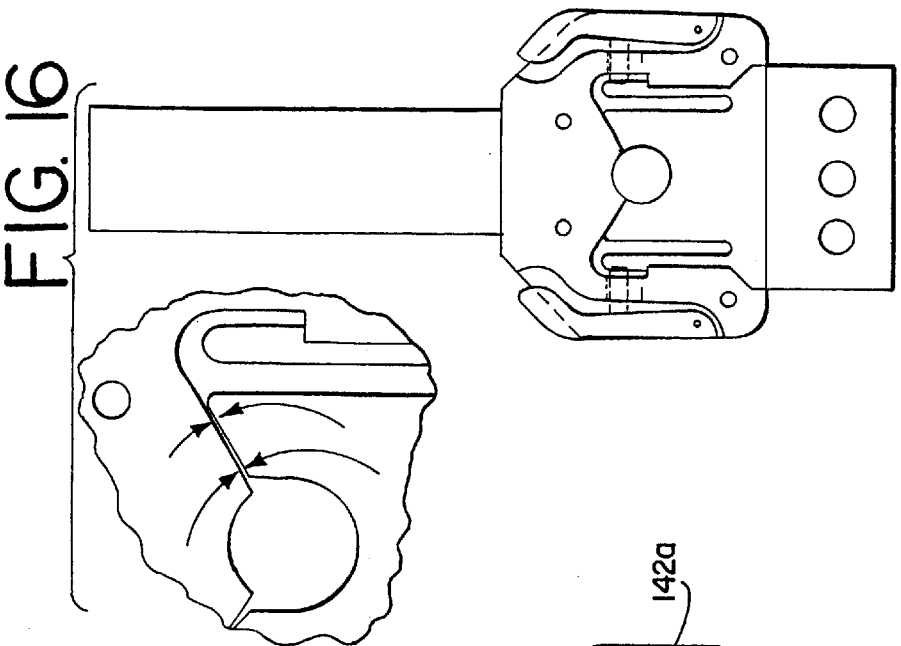
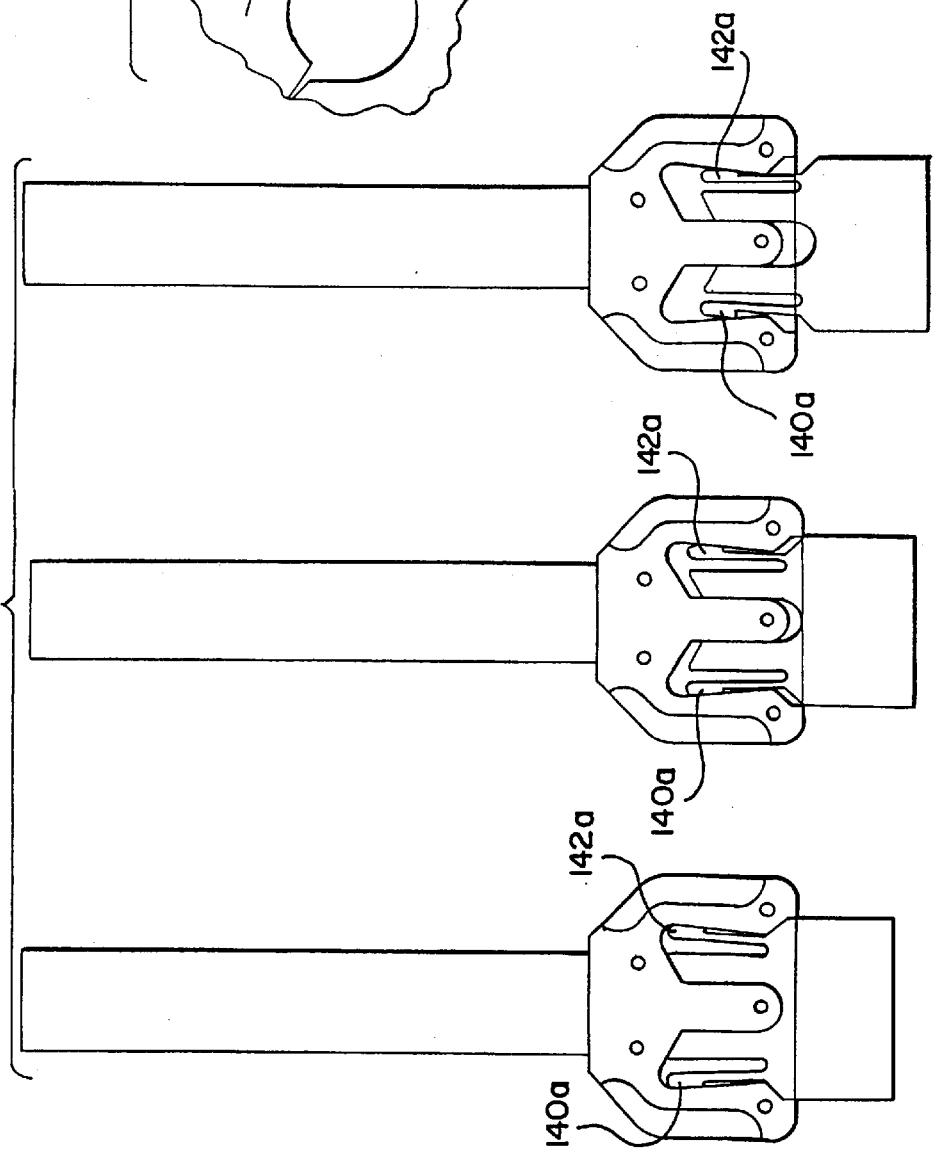

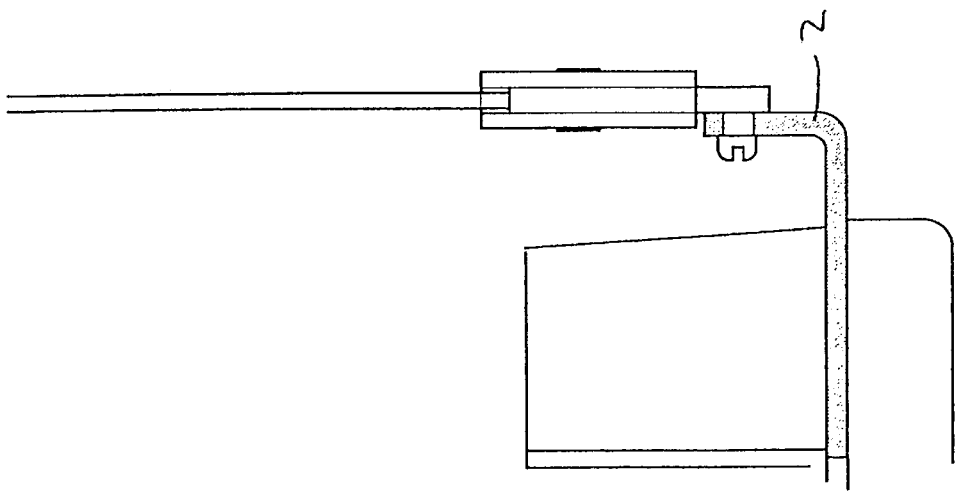

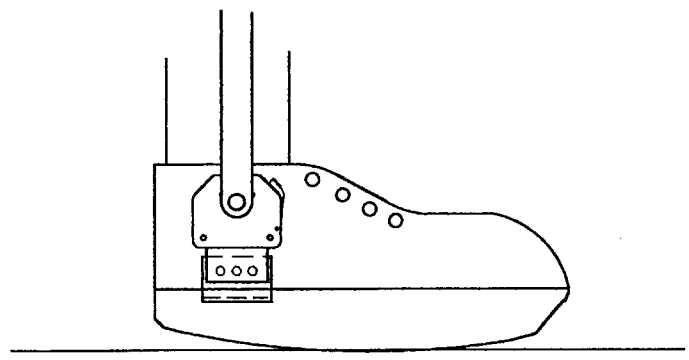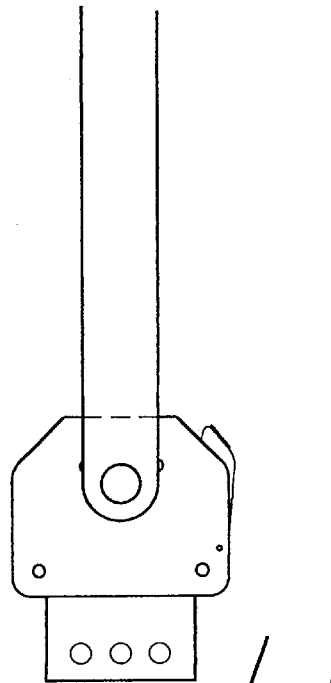
FIG. 21a
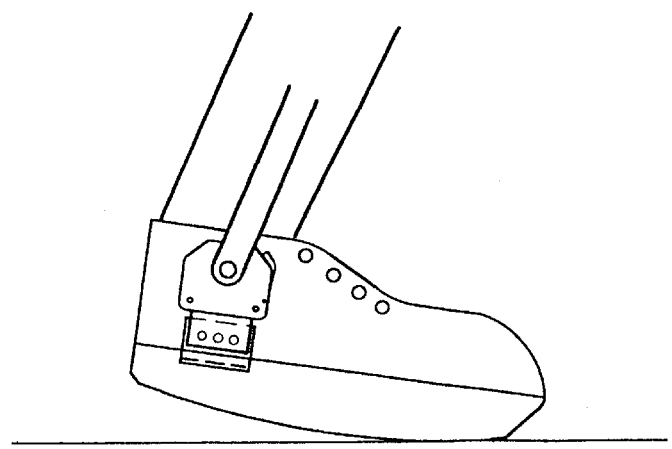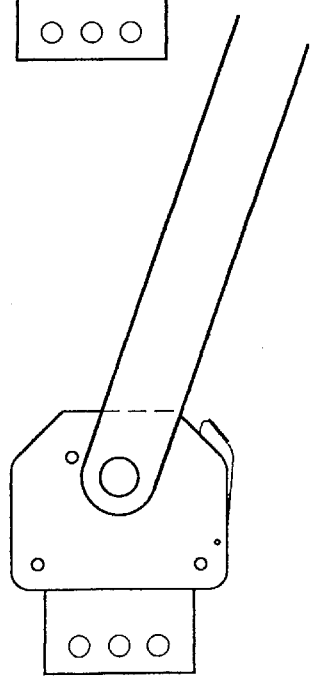
FIG. 21b

QUICK RELEASE MECHANISM FOR ORTHOPEDIC LIMB BRACE

CROSS REFERENCE TO RELATED APPLICATION

This is a continuation-in-part of parent application number 08/503,197 filed Jul. 17, 1995, now U.S. Pat. No. 5,851,194 issued on Dec. 22, 1998.

This invention relates generally to orthopedic braces, and more particularly, to a quick release orthopedic brace joint, specifically a quick release orthopedic brace ankle joint.

BACKGROUND OF THE INVENTION

Orthopedic braces are generally categorized as precision medical appliances, designed to be assistive devices for disabled people. Many types of braces exist for different applications. Generally prescribed by a doctor and built by an orthotist, the brace is built to solve a specific medical problem. Problems such as longevity and integrity of the human joint(s), compensation of limb length differences, etc. are addressed, but very often the function of a brace as it pertains to the medical condition is the primary focus. Therefore, the design of the brace may not take into consideration the user or patient in terms of user convenience, comfort, aesthetics, or component quality and durability. Often, the user has few or no options, other than to wear the brace or not wear it. The overall design and concept of the metallic orthopedic brace has not substantially changed in fifty years.

Design, quality and fit are keys to the proper operation and function of a brace. When any one of these is inadequate, the brace will not be useful or comfortable to the user. However, the brace must still be used regardless of fit or comfort because it is necessary for the medical needs of the user. Further, as the brace components wear, the originally provided support is greatly reduced, and the fit becomes worse. The result to the user can be pressure sores, ulcers or break down of the limb. These sores or ulcers can be very serious and can severely affect the health and lifestyle of the patient. Patients that must wear an orthopedic appliance may not have feeling in the particular limb, and the awareness of a problem; sores, infections, etc. is not realized until the brace is removed, generally at the end of the day.

The standard design of the orthopedic ankle brace (described in more detail below) includes a stirrup mounted in the sole of a shoe. The stirrup then is fastened via screws to the upper portion of the brace. This standard design of the orthopedic ankle brace does not allow the user to easily remove the shoe/stirrup from the brace. Typically, problems such as ulcers or open sores can occur in the foot-ankle area where constant relative motion or rubbing occurs between the foot and shoe due to rubbing during use.

Although orthopedic shoes are generally "cast" to the foot, enough clearance (caused by temperature swelling of the foot and/or shoes) still exists for abrasive "rubbing". When the user's medical condition is a fused ankle, little or no ankle movement or rotation of the foot can occur. When the patient wears the brace, every step causes rotation between the shoe/stirrup and the brace, creating the relative movement or "rubbing" between the foot and shoe. When the brace components are new, the rotational movement which causes the rubbing may be slight, but as the joint components quickly wear the movement problem is magnified and the "rubbing" action becomes excessive.

The standard design for fastening the shoe to the brace is simply a screw or locknut or T-nut coupling the brace to the shoe/stirrup (see prior art FIGS. 1 and 2). The stirrup is installed within the shoe sole and becomes an integral part of the shoe. This fastening method is standard within the orthopedic industry and allows component interchangeability between the various manufacturers.

This standardization leaves little flexibility for the user, making it extremely difficult (almost impossible for the user while wearing the brace) to readily remove the shoe as a convenience option, or more importantly to check the foot for ulcers, or other potential problems. Proper operation of a screwdriver is impossible at the position and angle required when wearing the brace and the user chances the screwdriver slipping from the screw into the foot. Equally difficult is the insertion and removal of the nut while trying to insert and align the stirrup and upright member of the brace.

FIG. 1 is a partial cross sectional view which illustrates the standard fixed ankle brace/shoe relationship and how the "rubbing" occurs. FIG. 2a shows the prior art shoe and brace in the standing upright position or a relative position of ninety degrees. FIG. 2b shows the undesired rotation of the prior art brace joint as the user takes a normal stride. Due to the nature of this standard design, the T-nut and screw create a fulcrum to the body's mass and the shoe rotation occurs around this pivot point. Due to the flexibility of the human body, the brace, even when properly secured, is not a rigid part of the leg, and any excess "play" between the leg and brace will generate problems. As the rotation progresses (FIG. 2b), the upright of the brace is no longer parallel to the user's leg.

FIG. 2b also illustrates how the rotation occurs perpendicular to the joint, and the movement is limited only by the upper corner of the brace slot. The result is point contact between the stirrup and the upright which generates excessively high stresses at the upper corner of the stirrup slot. These high stresses promote accelerated component wear and harmful rotation, and quickly increase the potential of undesired "rubbing". For a fixed ankle patient, it is very important that the brace pivot (screw and T-nut) be exactly in line with the patient's ankle joint. If not, the rotation that does occur will be around more than one point, and may cause more problems.

Another major problem of this standard design is, as the components wear, the structural integrity of the brace diminishes. This often leads to problems such as the user falling or tripping due to the instability of the brace and shoe. Such a situation can cause the user to further suffer from sprains or even broken bones.

There have been attempts made to solve some of the above mentioned problems. For example, U.S. Pat. No. 3,064,644 issued to Patterson on Mar. 2, 1960 discloses a lower leg brace designed to aid the user in "toe pickup". As the user takes a step, the secondary hardware (springs, balls and push rods) generate a force greater than the weight of the foot and assist the foot and ankle into position for the next step. One object of Patterson is to be able to remove the stirrup from the leg brace. The insertion process requires the solid tongue (items 6 and 8) to slide into the stirrup and lock into position. The secondary spring and rod pressure helps to hold the tongue within the stirrup. In order for the tongue to be inserted in the stirrup, an insertion angle requiring a large dimensional difference between the tongue and stirrup must exist (FIG. 3). The resulting "play" within these parts results in unwanted movement between the shoe and brace as described earlier. Secondary screws, springs, balls and rods are required to complete this assembly. The end product is heavy, bulky and not "self contained" unlike the present invention. The present invention is much more compact, uses geometry for a precision fit, and uses the inert properties of the metal to create the spring required to connect and disconnect the shoe and stirrup. The present invention requires no secondary hardware as does the Patterson device.

U.S. Pat. No. 2,934,064 issued to Invidiato on Apr. 13, 1954 discloses a surgical brace intended to fit within the shoe of a user. Invidiato does not disclose the brace being connected to, or quickly released from, the shoe. The present invention is designed to be attached to, and quickly released from, the user's shoe.

U.S. Pat. No. 874,446 issued to Slater on Jan. 21, 1907 discloses a brace wherein a wing nut is used to secure the brace to the stirrup. This device is intended to be a surgical splint and has no similarity to the present invention.

U.S. Pat. No. 4,646,726 issued to Westin, et al. on Nov. 6, 1985 discloses an ankle joint strap orthosis and is not a brace-shoe device unlike the present invention. Westin, et al.'s orthosis has no similarity to the present invention.

U.S. Pat. No. 3,454,002 issued to Westlake, et al. on Feb. 28, 1966 discloses an orthopedic splint and has no similarity to the present invention.

U.S. Pat. No. 2,516,872 issued to Hauser. et al. on Jan. 27, 1948 discloses a brace wherein the wearer may change his shoes without removing the brace from his leg. The design of the Hauser, et al. brace requires the use of secondary components to achieve the disconnecting function. One side of the Hauser, et al. brace uses a guide pin which slides into the stirrup and is retained by a pivoting arm that is screwed to and pivots from the upright portion of the assembly. The release mechanism is a lever located on the opposite side of the brace. The lever (25), which is pivoted from the upright, slides into a recessed area of the stirrup after insertion. The forces are transferred entirely through the opposite pin and slide since the locking lever has no means to retain it in the locked position. The forces on the brace would tend to open the lever as the user takes a normal stride. This is especially true when the parts begin to wear. Further, the connect and disconnect process is almost as difficult as the shoe removal from a standard brace. The Hauser, et al. device is bulky, requires many parts, is not self contained and the parts are not interchangeable to either side of the shoe or brace.

The present invention solves the problems and shortcomings of the above mentioned prior art devices.

BRIEF SUMMARY OF THE INVENTION

The present invention is a quick release orthopedic brace ankle joint designed to alleviate the ulcers, and potential disabling injuries caused by the standard brace ankle joint. The quick release mechanism of an ankle joint of the present invention allows the user to easily remove the shoe from the brace even while being worn. One embodiment of the present invention has no or very limited unintentional rotation during use, and is designed to function better as the parts began to wear. The present invention is a completely self-contained unit and functions without the need of supplementary hardware.

The present invention comprises two basic assemblies and several subassemblies. The upright assembly consists of the main frame or clip housing, two release bars, two side plates, and a main support pin. The clip member is the second main component, and can be manufactured as a full stirrup or as a separate component that can be retrofitted to a user's existing brace. The clip and stirrup are fastened to the shoe sole and are the supporting and disconnecting means of the shoe to the brace. The unique geometric design of the present invention allows the clip member to be inserted and removed from the upright assembly without the necessity of other springs, removable hardware, etc. The present invention can be embodied in many forms, for example a fixed clip, a pivoting clip, and a limited rotation clip depending on the medical needs of the user.

Accordingly, it is the principle object of the present invention to provide an orthopedic limb brace.

It is the further object of the invention to provide a quick disconnect joint for an orthopedic brace.

It is also the object of the present invention to provide an orthopedic brace that is easy to use by one person (the wearer).

It is an additional object of the invention to provide an orthopedic ankle brace that provides easy change of shoes while wearing the brace.

It is still a further object of the invention to provide a quick disconnect joint for an orthopedic brace that minimizes the occurrence of ulcers or sores caused by standard braces.

It is another object of the invention to provide a quick disconnect joint for an orthopedic brace that minimizes potential injuries or disabilities during use.

It is yet another object of the invention to provide a quick disconnect joint for an orthopedic brace that maintains the doctor-prescribed integrity of the human joint.

It is still another object of the invention to provide a quick disconnect joint for an orthopedic brace that is designed to minimize wear and maintain the structural integrity of the brace.

It is still another object of the invention to provide a quick disconnect joint for an orthopedic brace that has no loose parts or other hardware.

It is still another object of the invention to provide a quick disconnect joint for an orthopedic brace that is aesthetic, light weight, and interchangeable to either side of the brace.

Numerous other advantages and features of the invention will become readily apparent from the detailed description of the preferred embodiment of the invention, from the claims, and from the accompanying drawings in which like numerals are employed to designate like parts throughout the same.

BRIEF DESCRIPTION OF THE DRAWINGS

A fuller understanding of the foregoing may be had by reference to the accompanying drawings wherein:

FIG. 1 is a partial cross sectional view of a prior art ankle brace illustrating the attachment of the same;

FIG. 2a is a side view of the prior art device of FIG. 1 shown in use in a normal standing position;

FIG. 2b is a side view of the prior art device of FIG. 1 shown in use in a normal striding position;

FIG. 4 is a front elevational view illustrating the present invention of FIG. 3a being connected;

FIG. 5 is a front elevational view of the present invention of FIG. 3a in a connected position;

FIG. 7 is a front elevational view of the clip portion of the present invention of FIG. 3a;

FIG. 8 is a front elevational view of the clip housing portion of the present invention of FIG. 3a;

FIG. 9 is an exploded view of an alternate embodiment of main support pin of the present invention of FIG. 3a;

FIG. 12 is an exploded view of an alternate embodiment of the brace joint of the present invention;

FIG. 13 is a front elevational view illustrating the present invention of FIG. 12 in a connected position;

FIG. 15 is a front elevational view illustrating the present invention of FIG. 12 being connected;

FIG. 16 is an enlarged front view of the present invention illustrating the initial clearances between the clip and frame;

FIG. 18b is a side view of the view illustrated in FIG. 17 illustrating the attachment of the same;

FIG. 21a is a side view of the present invention of FIG. 19 in use in a normal standing position;

FIG. 21b is a side view of the present invention of FIG. 19 in use in the end of a normal striding position;

DETAILED DESCRIPTION OF THE PREFERRED EMBODIMENT OF THE PRESENT INVENTION

Figure 3A:
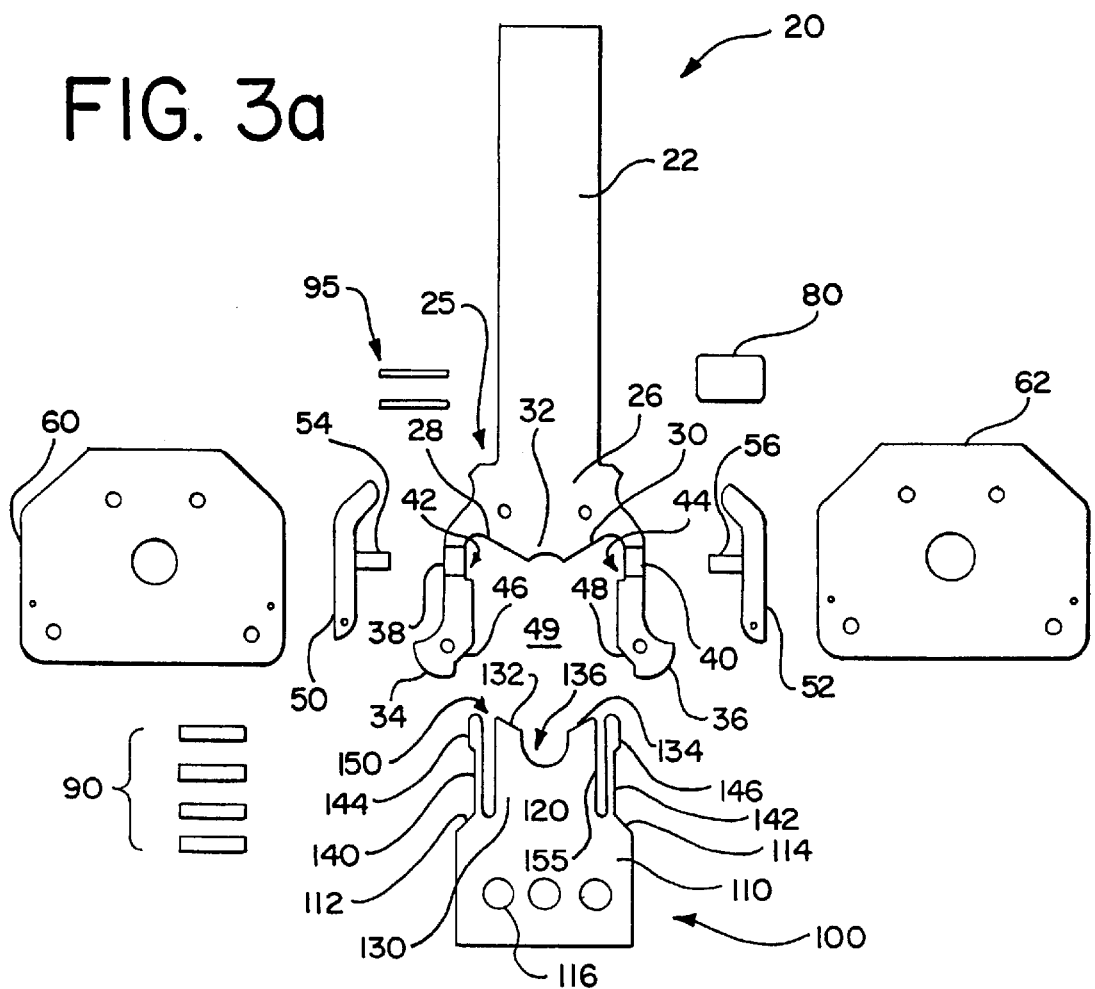
FIG. 3a is an exploded view of the brace joint of the present invention.

While the invention is susceptible of embodiment in many different forms, there is shown in the drawings and will be described herein in detail, preferred embodiments of the invention. It should be understood, however, that the present disclosure is to be considered an exemplification of the principles of the invention and is not intended to limit the spirit and scope of the invention and/or claims of the embodiment illustrated.

FIG. 1 shows a partial cross-sectional view of a prior art ankle brace as seen from the backside of shoe 1. As can be seen, this prior art ankle brace consists of a stirrup 2 mounted in the sole of shoe 1 and an upright member 3 having a stirrup slot 4. Stirrup slot 4 comprises a first arm 5 and a second arm 6. The upturned portion of stirrup 2 is received within stirrup slot 4 and the upright member is fastened to the stirrup by means of a screw 7 and a T-nut 8. However, this prior art ankle brace has the problems and disadvantages as mentioned previously and as better seen in FIGS. 2a and 2b.

FIG. 2a illustrates the prior art ankle brace in use by a user standing in a normal position wherein the brace is perpendicular to the ground surface and the shoe. As can be seen in FIG. 2a, the upturned portion of stirrup 2 is received in stirrup slot 4 of the upright member 3. When the user takes a normal stride, as illustrated in FIG. 2b, rotation occurs relative to the upright member and the stirrup, as is illustrated. The upper edge corner of the upturned portion of stirrup 2 contacts the top of the stirrup slot 4 at point A. As a result of such rotation, a high stress and wear area occurs at the point of contact A between the top of stirrup 2 and the top of the slot 4.

FIGS. 3 through 21 illustrate the present invention 10, as well as alternate embodiments of the present invention.

FIG. 3a illustrates the present invention 10 comprising an upright assembly 20 and a clip 100. Upright assembly 20 includes an upright member 22 having a main frame or clip housing 25 integrally mounted at an end thereof. Upright assembly 20 further comprises release bars 50 and 52, side plates 60 and 62 and a main support pin 80.

Main frame or clip housing 25 comprises a middle section 26, a first arm 34, and a second arm 36. First arm 34 and second arm 36 depend from middle section 26 to form a generally C-shaped opening 49. Middle section 26 includes sloped surfaces 28 and 30 and a notch 32 formed at the ends of sloped surfaces 28 and 30. First and second arms 34 and 36 include bores 38 and 40 respectively and recessed portions 42 and 44 respectively. Further, first and second arms 34 and 36 have interior sloped end surfaces 46 and 48.

Release bars 50 and 52 include striking pins 54 and 56 at a mid portion thereof. Release bars 50 and 52 are mounted to first arm 34 and second arm 36 respectively by release bar pivot pins 95. The release bars 50, 52 pivot approximately five degrees and are assembled within the side plates by pivot pins 95. Side plates 60 and 62 are mounted to the main frame or clip housing 25 by assembly pins 90 which are pressed fit and peened flush.

Main support pin 80 is mounted in notch 32 and between side plates 60 and 62, thus enclosing the sides of C-shaped opening 49. The main support pin 80, also pressed fit and peened to the side plates 60, 62, functions as a guide/bearing support to the clip 100, and provides additional support for the entire assembly.

Clip 100 of the present invention includes a main portion 110 and a tongue portion 120. Main portion 110 includes mounting bores 116 for attachment to the upturned portion of a stirrup mounted in the sole of the user's shoe. Portion 110 further includes sloped side surfaces 112 and 114. Tongue portion 120 includes a central flange 130, a first locking member or leaf spring 140, and a second locking member or leaf spring 142.

Central flange 130 includes sloped surfaces 132, 134 and notch 136. First locking member or leaf spring 140 includes a head portion 144 and second locking member or leaf spring 142 includes a head portion 146. Slots 150 and 155 are provided between the first and second locking members 140, 142 and the tongue portion central flange 130 to allow the leaf springs to flex, pivot, or deform upon insertion and removal of the clip into the clip housing.

Figure 3B:
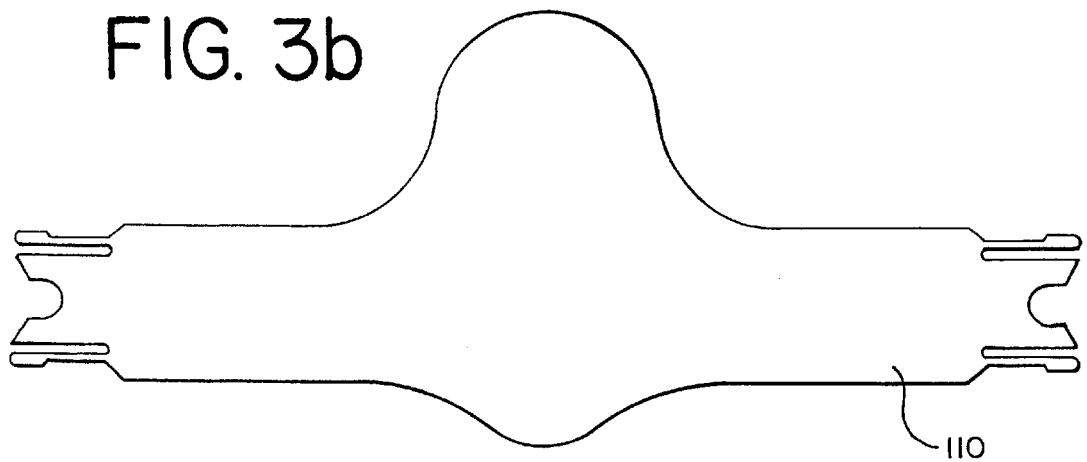
FIG. 3b is a flattened view of an alternate embodiment of the clip portion of the present invention.

FIG. 3b shows an alternate embodiment of the clip of the present invention wherein the clip is integrally formed with the stirrup. Main portion 110 of the clip does not include mounting bores 116, but rather is integral with the upturned portion of the stirrup (shown flattened) mounted in the user's shoe.

FIG. 4 illustrates the present invention wherein the clip 100 is being inserted into the clip housing 25 to connect the brace to the user's shoe. Tongue portion 120 of clip 100 is inserted into the C-shaped opening 49. First locking member and second locking member 140, 142 deform into slots 150 and 155 respectively, and ride up along the interior sides of first and second arms 34 and 36, until head portions 144 and 146 engage the recessed portions 42 and 44 of arms 34 and 36 to lock clip 100 into clip housing 25.

FIG. 5 illustrates clip 100 in a locked position in clip housing 25. As can be seen, sloped side surfaces 112 and 114 of clip 100 mate with the interior sloped end surfaces 46 and 48 of arms 34 and 36 of the clip housing 25. Further, slopes 132 and 134 of central flange 130 of tongue portion 120 mate with the sloped portions 28 and 30 of middle section 26 of clip housing 25. Main support pin 80 is received within notch 136 of the central flange 130 of tongue portion 120. Head portions 144 and 146 rest in the recessed portions 42 and 44 of arms 34 and 36 to effectively lock the user's shoe to the upright member 22 and prevent relative rotation in the joint. A clearance is provided between the bottom portion of the spring leaf head potions 144 and 146 and the bottom surface of recessed portions 42 and 44. This clearance is to assure that the spring leafs 140 and 142 will not be sheared from the clip 100 if slight rotation occurs between the frame and clip (due to machining tolerances, etc.). The spring leafs do retain the clip 100 to the upright member 22, however, as the user takes a stride, the weight and forces are compressive and force the clip and frame together at the main pin or tongue and the four sloped areas.

Figure 6A:
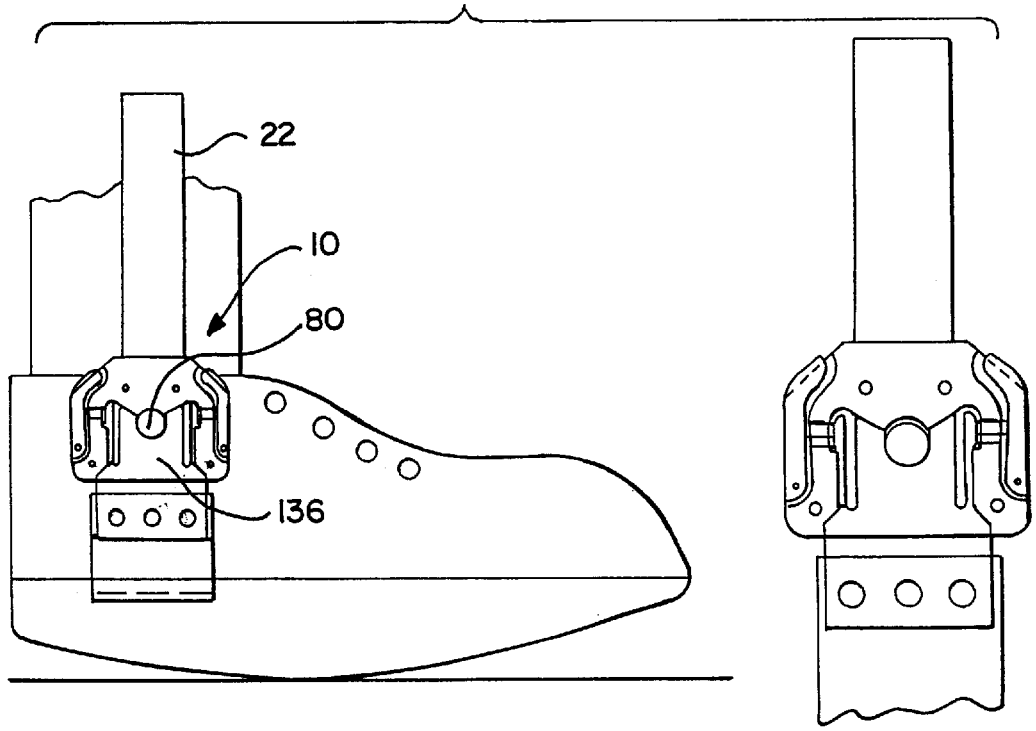
FIG. 6a is a side view of the present invention of FIG. 3a in use a normal standing position.
Figure 6B:
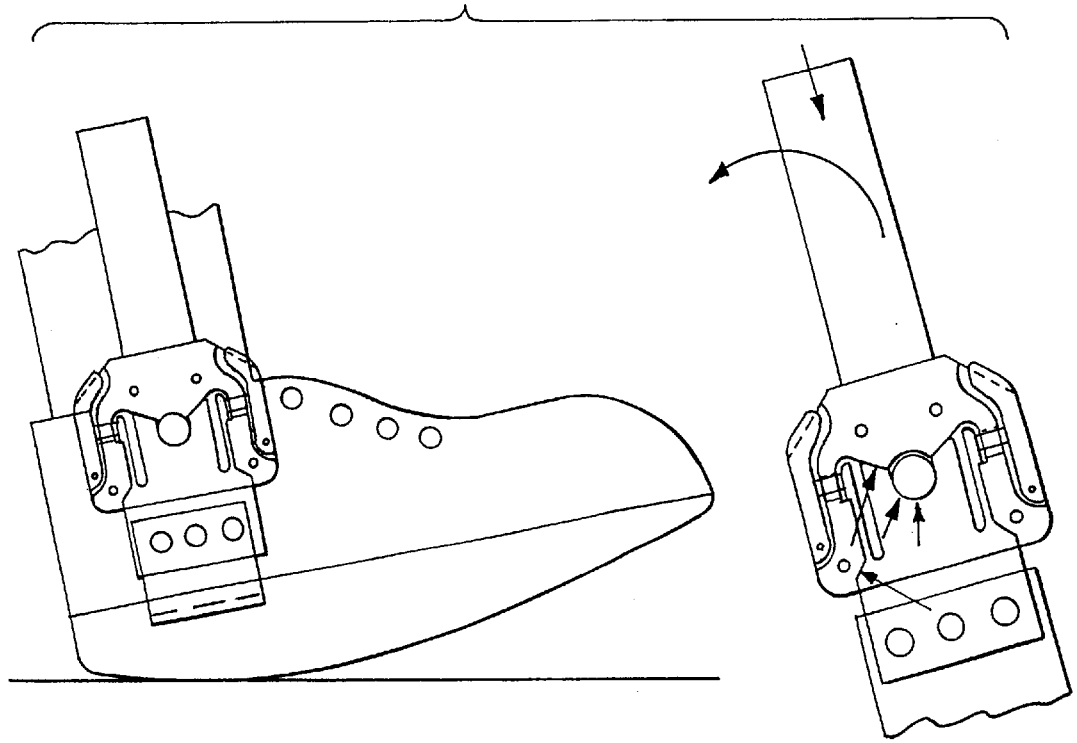
FIG. 6b is a side view of the present invention of FIG. 3a in use in the beginning of a normal striding position.
Figure 6C:
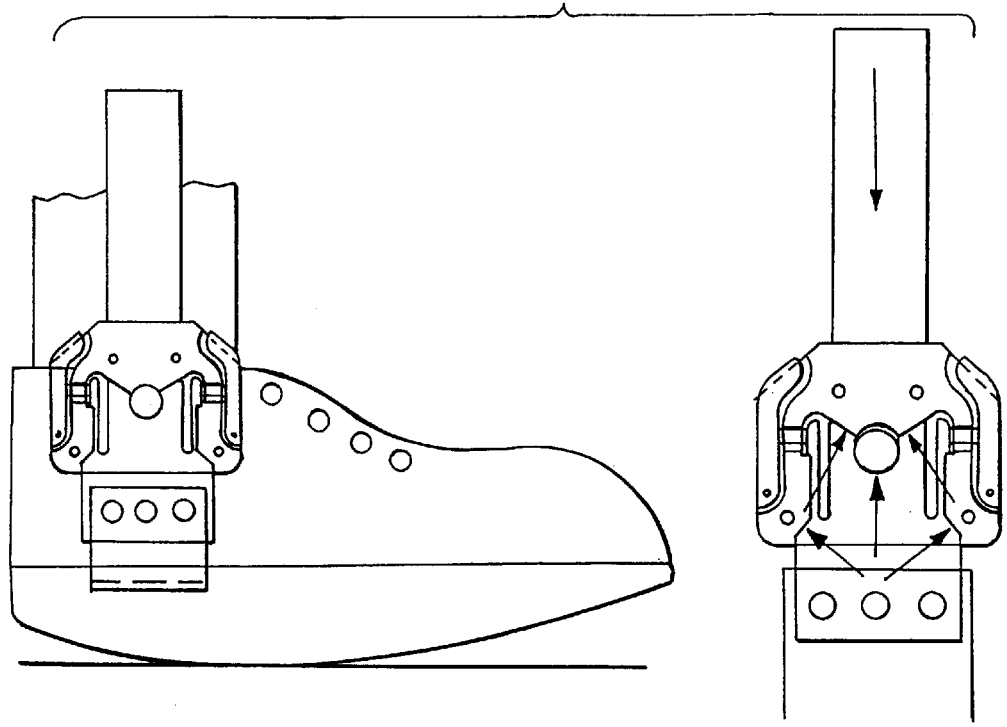
FIG. 6c is a side view of the present invention of FIG. 3a in use in the middle of a normal striding position.
Figure 6D:
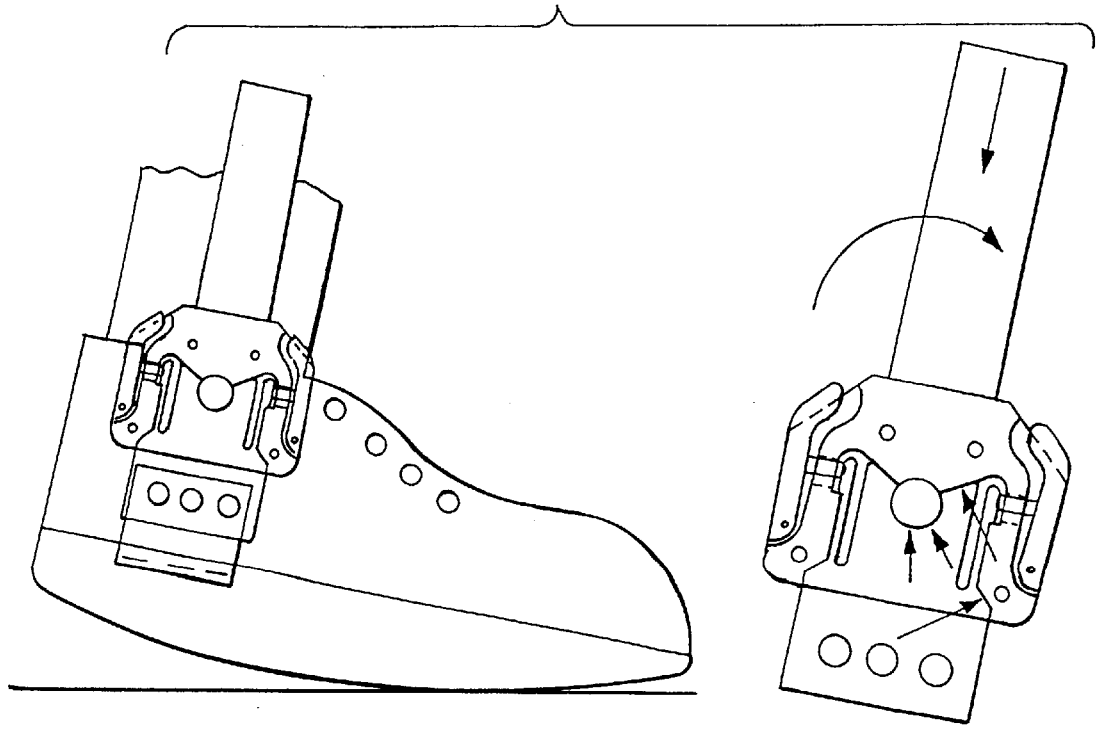
FIG. 6d is a side view of the present invention of FIG. 3a in use in the end of a normal striding position.

FIG. 6a is a side view of the present invention 10 in use in a normal standing position wherein the upright member 22 of invention 10 is perpendicular to the user's shoe and the ground surface. When the user takes a normal stride as illustrated in FIGS. 6b–6d, the upright assembly and the stirrup rotate together due to the interlocking of the clip housing 25 and clip 100. As the clip slot or notch 136 bottoms out against the pin 80, the four mating surfaces or sloped areas on the clip are also mated with respective four sloped areas on the clip housing. As the user takes a stride, the geometry of the clip/frame allows the resultant forces (illustrated as arrows in FIGS. 6b–6d) to be transferred to the sloped areas of the frame in the direction of impending rotation. These forces are then distributed through the assembly pins, side plates and to the rest of the brace.

The fixed embodiment of the present invention was designed for users with a fixed or fused ankle. Due to the flexibility of the natural foot, the fused limb retains a certain amount of movement. This movement or roll within the joint, along with other foot and leg motions during the stride create complex configurations between the foot, shoe and brace. The present invention is designed to help compensate for these configurations. As the user begins the stride (FIG. 6b), the foot and shoe approach the ground from an angle relative to the length of the stride. As the shoe strikes the ground, forces (indicated by arrows) are generated and transferred through the ankle joint. The main pin or tongue and sloped areas transfer the forces to the frame and side plates. During this first portion of the stride, the design tolerances between the clip and frame's sloped areas allow a slight amount of roll on the main pin or tongue. This roll allows the rear portion of the clip and frame to mate and distribute the forces of the initial impact to the rest of the brace. The sloped areas of the clip and frame are at slightly different angles when new. As the joint is used, normal wear allows the surfaces to mate precisely ensuring a properly-fitting joint for the user. As the stride is continued (FIG. 6c), the clip again rolls slightly along with the user's foot and leg. The forces (indicated by arrows) are all compressive and become equally distributed on the sloped areas and pin or tongue at mid stride. Up to this point, the geometry of the joint has transmitted most of the forces to the brace and not the foot. For proper protection of the foot, it is critical for the joint and brace to absorb as much of the generated forces as possible. During the last phase of the stride (FIG. 6d), the user's body moves forward of the foot. The clip and frame again roll slightly and allow the opposite sloped areas to mate. As the frame mates with the clip, the forces are distributed to the side plates and to the rest of the brace. During this phase, the generated forces (indicated by arrows) are basically torsion and compression caused by the forward movement and user's weight. As the user begins the follow through portion of the stride, the forces in the joint are relaxed and the clip can roll slightly with the foot and shoe, as all stresses are relieved to begin the next cycle. Throughout the entire stride, the ankle joint must protect the foot by absorbing the shock and various forces created. Although the present invention was designed as a quick release fixed ankle joint, the unique design also allows it to roll slightly with the user's foot, protect the foot from the impacts and forces of the stride, and actually function better as the joint wears.

FIG. 7 illustrates the clip portion 100 of present invention 10. Clip 100 includes main portion 110 having sloped side surfaces 112 and 114 and mounting bores 116. Clip 100 further includes tongue portion 120 having central flange 130, first locking member 140, and second locking member 142. Slots 150 and 155 exist between first locking member 140 and central flange 130 and second locking member 142 and central flange 130 respectively. Slots 150 and 155 are cut behind the leaf springs 140, 142 to allow for flexing movement and are radiused at the main portion 110 to minimize stress. As can be seen, central flange 130 has sloped surfaces 132 and 134 and notch 136. It is foreseen that one leaf spring and one release bar is sufficient for the proper operation of the present invention, thus allowing for an even quicker release of the brace mechanism.

FIG. 8 illustrates the upright member 22 integrally connected to the main frame or clip housing 25. Clip housing 25 includes middle section 26 having sloped surfaces 28 and 30 and a notch 32. Clip housing 25 further includes first arm 34 and second arm 36 opposite first arm 34 and defining a C-shaped opening 49. First and second arms 34 and 36 include bores 38 and 40 for receiving the striking pins 54 and 56 of release bars 50 and 52 respectively. First and second arms 34 and 36 further include recessed portions 42 and 44 for receiving the head portions 144 and 146 of first and second locking members 140 and 142 respectively. First and second arms 34 and 36 also include interior end sloped surfaces 46 and 48. Mounting bores can also be seen to receive assembly pins 90 to mount side plate 60 and 62 to form upright assembly 20.

FIG. 9 illustrates an alternate embodiment of the main support pin or tongue 80a, wherein the pin 80a is machined or integrally formed with the clip housing 25. Since placement of the pin is critical to the operation of the device, machining or cutting the tongue 80a into the frame 25 will simplify assembly and assure dimensional accuracy. The tongue 80a performs the same function as the pin 80, however, the tongue 80a can be made to various lengths. The tongue 80a will also serve to secure the joint assembly 20. The tongue will have a hole drilled to accept an additional assembly pin 90 identical to the other four pins 90, for a total of five pins per assembly. The clearances provided for this configuration are the same as the main support pin 80 of FIG. 3a. Clip 100 contains notch 136a for receiving tongue 80a.

FIGS. 10–11 and 17–21 illustrates alternate embodiments of the present invention wherein upright assembly comprises an upright member 22 which is not integrally connected with clip housing 25, but is instead pivotable. The pivotal embodiments of the present invention are designed for patients that have a normally rotating ankle, yet need to wear a brace as prescribed by a doctor. The design concept is similar to the embodiments of FIGS. 1–9, however, there are several component differences.

Figure 10:
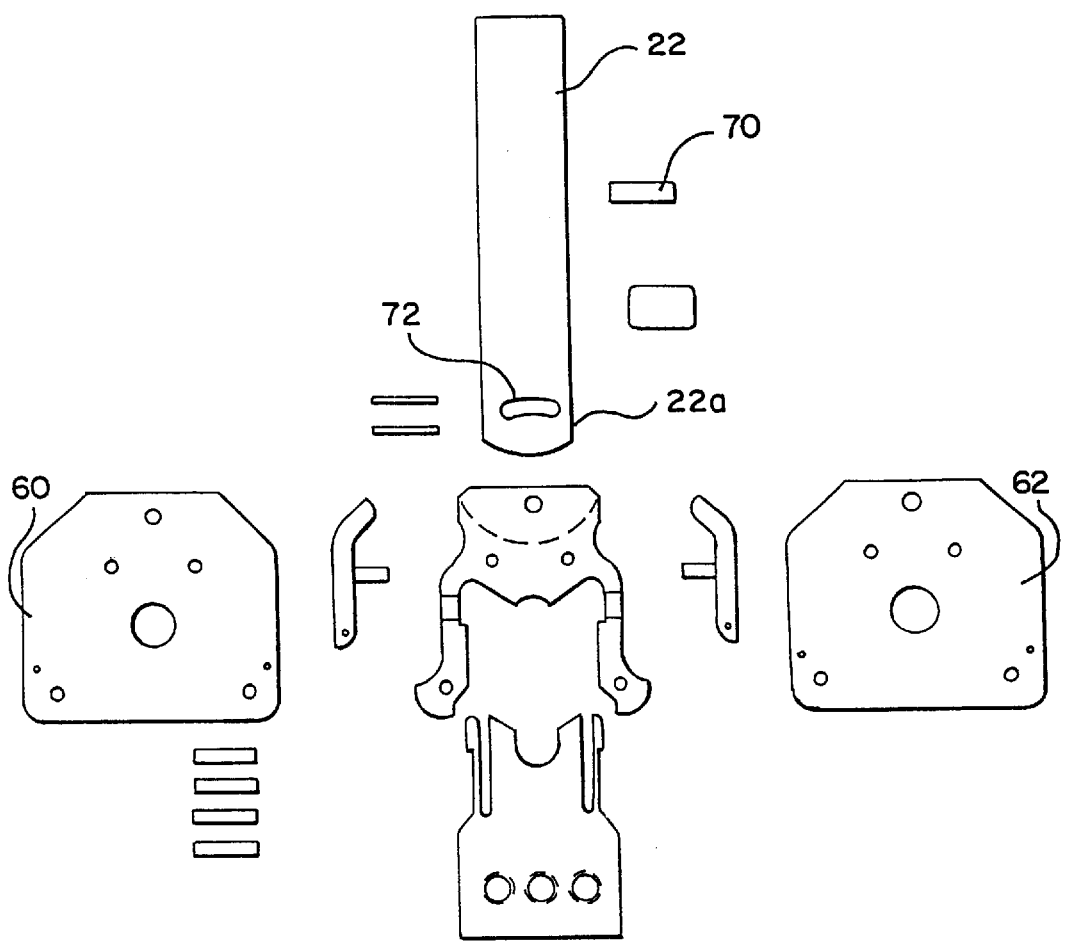
FIG. 10 is an exploded view of an alternate embodiment of the brace joint of the present invention.
Figure 11A:
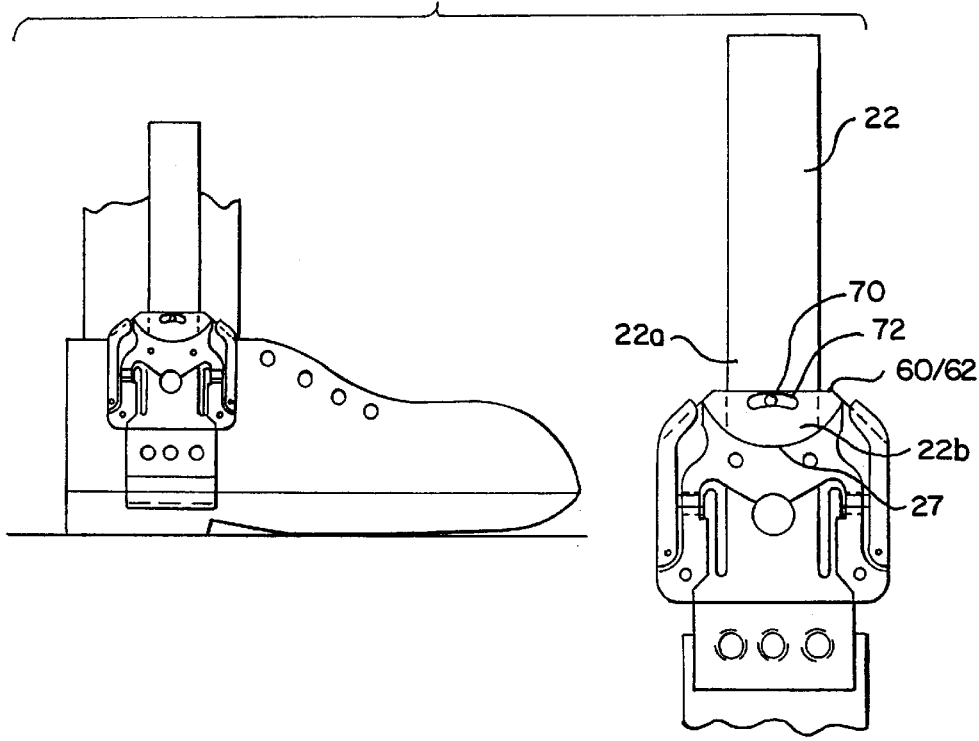
FIG. 11a is a side view of the present invention of FIG. 10 in use in a normal standing position.
Figure 11B:
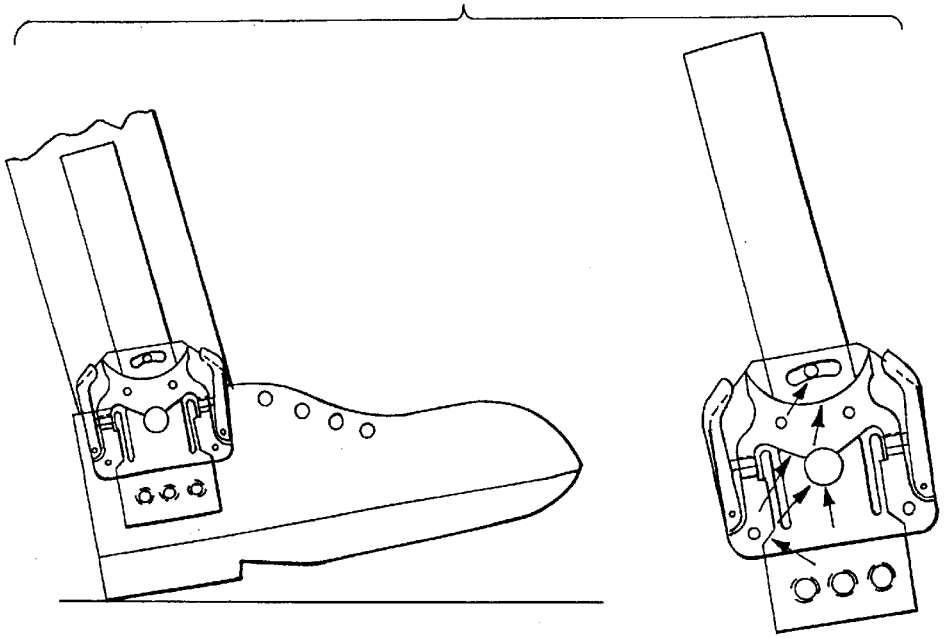
FIG. 11b is a side view of the present invention of FIG. 10 in use in the beginning of a normal striding position.
Figure 11C:
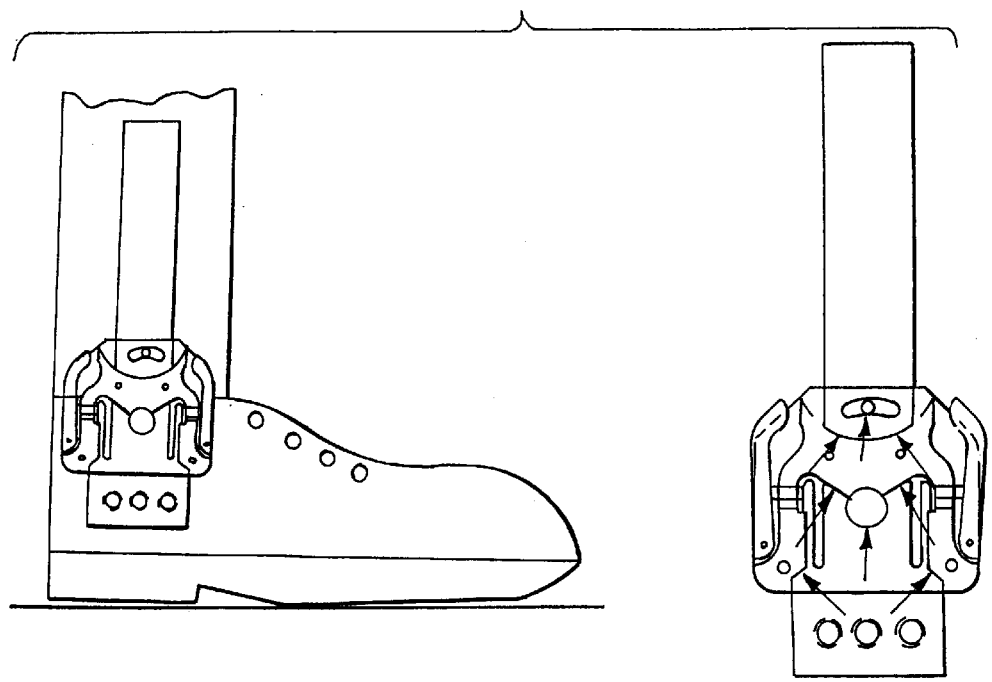
FIG. 11c is a side view of the present invention of FIG. 10 in use in the middle of a normal striding position.
Figure 11D:
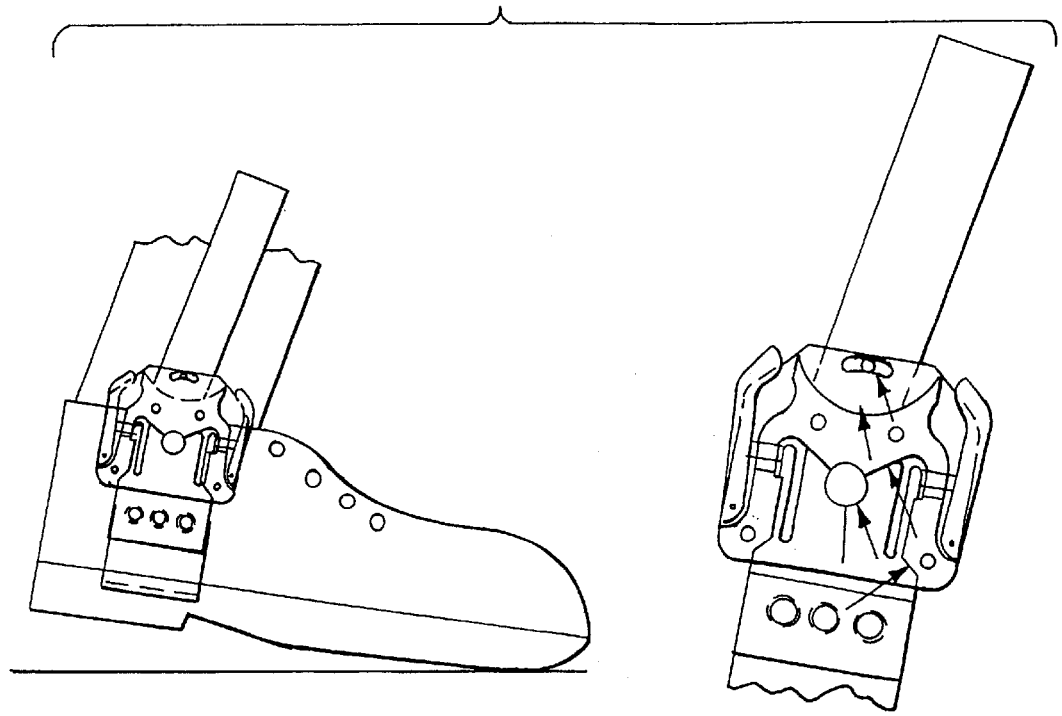
FIG. 11d is a side view of the present invention of FIG. 10 in use in the end of a normal striding position.

As seen in FIG. 10, the lower end 22a of the upright member 22 is lengthened and a pivot/bearing pin 70 is inserted in slot 72 in lower end 22a and mounted to frame 25 to allow the upright member 22 to pivot or rotate within the same radius as the user's ankle joint. The upright member 22 and main frame or clip housing 25 of this embodiment are separate parts and not one assembly as in the fixed version. The side plates 60, 62 are slightly longer to fit the elongated frame contour of frame 25 but the clip design remains the same.

As seen in FIGS. 11a–11d, the release concept of the pivotable embodiment is the same as the fixed embodiment with the frame 25 and clip 100 utilizing either the pin 80 or tongue 80a designs. The pivoting of the upright 22 and clip 100 occurs at the main pivot pin 70 location. The lower end 22a of upright 22 is assembled within the side plates 60, 62 and pivots on the main pivot pin 70. The main pivot pin 70 extends through the slot 72 and is supported by the two side plates 60, 62. The upright is contoured on the bottom 22b to match the frame arc contour 27, providing a mating or bearing/wear surface for the two components. This bearing surface creates even stress distribution and allows smooth rotational motion between the two parts. Although the actual rotation and movement occur at the main pivot pin 70 location, the center of rotation or radius is located at the center pin (main support pin) 80, or on the tongue version, the center of the tongue 80a. If only pure rotation is needed at the joint, the upright 22 would have just a clearance hole for the main pivot pin 70 instead of slot 72 which allows for slight lateral movement of upright 22 in addition to rotation movement. Two release bars are shown for this assembly, however, only one may be required for proper operation, as illustrated in FIGS. 17–21. Although the engineering concept is on the quick connect/release brace ankle joint, the basic clip design is flexible enough to encompass different variations or options to suit the user's requirements.

Figure 17:
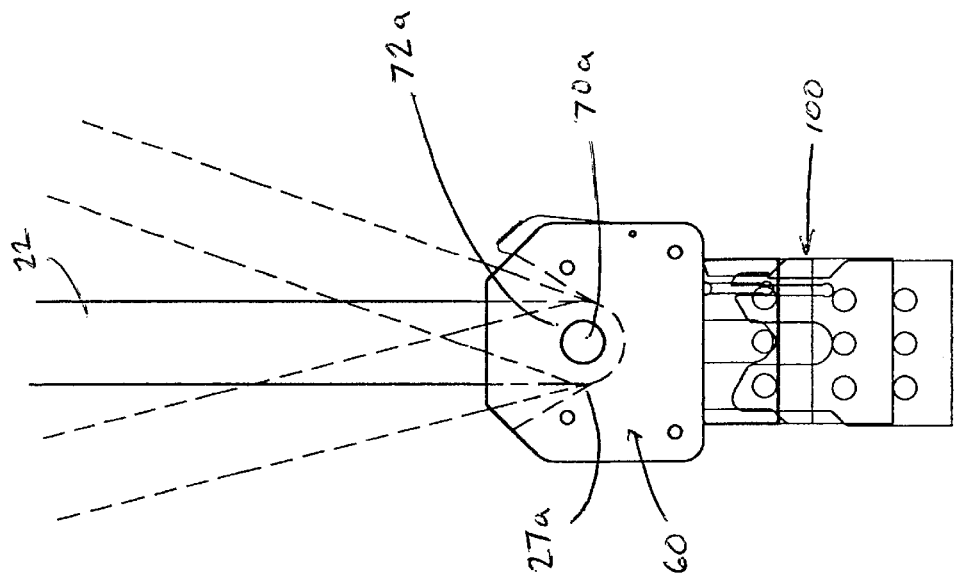
FIG. 17 is a side view of an alternate embodiment of the pivoting brace joint of the present invention.

FIG. 17 illustrates an alternate embodiment of the pivotal embodiment of FIG. 10. In this embodiment, upright 22 is provided with a clearance hole 72a and is pivotably mounted in the frame 25 by a pivot pin 70a. Frame 25 is provided with a radiused V-shaped cutout 27a within which upright 22 is free to pivot as illustrated in phantom. only one release bar is illustrated, however, two could be provided. The remainder of the clip 100, frame 25 and side plate assembly 60, 62 remain the same, with the exception of slight dimensional changes to accommodate the addition of the pivoting means. Pivot pin 70a could take the form of a screw and bearing-nut type assembly. The generated forces are transferred from the clip to the frame assembly and pivot pin, to the upright and then distributed through the rest of the brace.

Figure 18A:
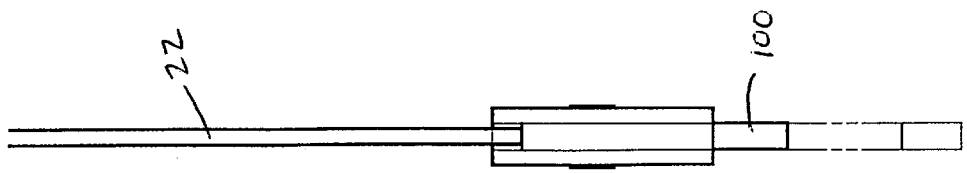
FIG. 18a is a side view of the view illustrated in FIG. 17.
Figure 18C:
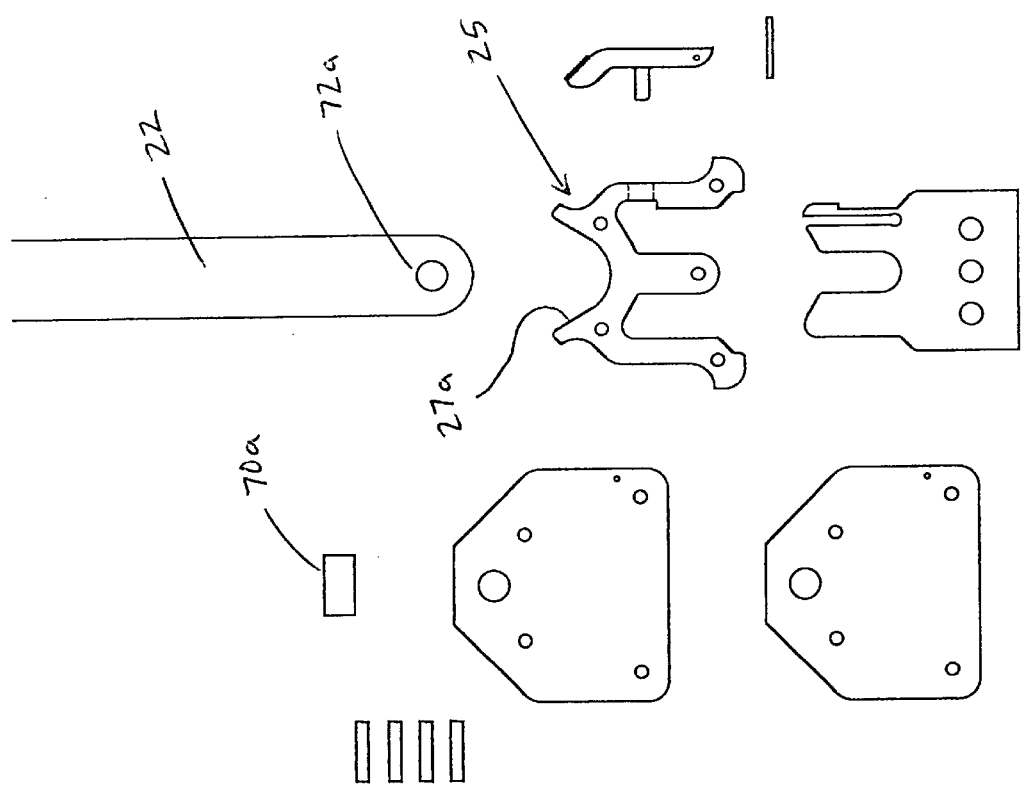
FIG. 18c is an exploded view of the view illustrated in FIG. 17.

FIG. 18a illustrates the pivotal embodiment of FIG. 17 from the side. FIG. 18b is the same illustration as FIG. 18a, but further illustrates connection of the clip 100 to stirrup 2. FIG. 18c illustrates an exploded view of the pivotal embodiment of FIG. 17. As can be seen, upright 22 includes a clearance hole 72a at the lower end thereof, which is pivotably mounted within V-shaped cutout 27a in frame 25. Pivot pin 70a pivotably secures upright 22 between the two side plates and within the V-shaped gcutout 27a. The clip and frame are illustrated as having only one locking member and one release bar, respectively.

Figure 19:
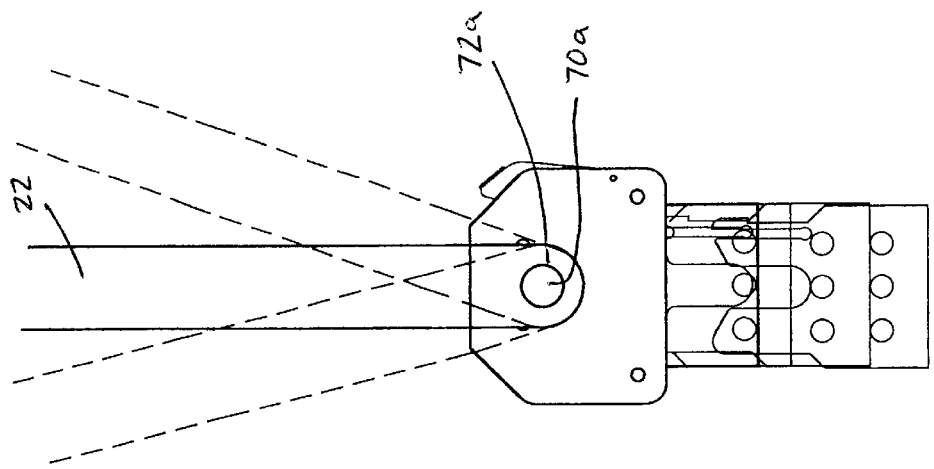
FIG. 19 is a side view of another alternate embodiment of the pivoting brace joint of the present invention.

FIG. 19 illustrates another alternate embodiment of the pivotal embodiment of FIG. 10. This embodiment is similar to that of FIG. 17, wherein upright 22 is provided with a clearance hole 72a and is pivotably mounted in the frame 25 by a pivot pin 70a. However, frame 25 is not provided with any cutout or arc contour. The upright 22 is mounted on the outside of frame 25 and side plate assembly. Optionally, the upright 22 includes a fork member 23 (FIG. 20a) to provide support and stability from both sides of the frame assembly. Thus, upright 22 is free to pivot along the side or sides of the frame and side plate assembly, as illustrated in phantom in FIG. 19. Only one release bar is illustrated, however, two could be provided. The remainder of the clip 100, frame 25 and side plate assembly 60 remain the same, with the exception of slight dimensional changes to accommodate the addition of the pivoting means. Pivot pin 70a could take the form of a screw and bearing-nut type assembly. The forces generated during the stride (FIGS. 21a–21c) are transferred from the clip to the pivot pin, to the upright (or upright and fork member) and then distributed through the rest of the brace.

Figure 20A:
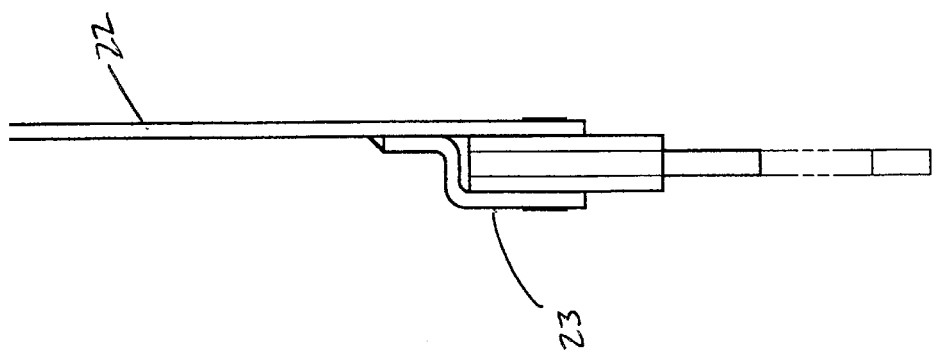
FIG. 20a is a side view of the view illustrated in FIG. 19.
Figure 20B:
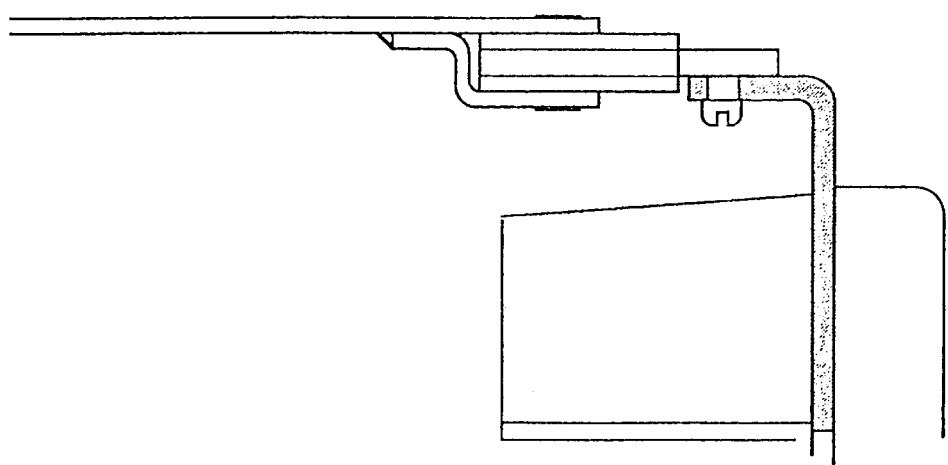
FIG. 20b is a side view of the view illustrated in FIG. 19 illustrating the attachment of the same.
Figure 20C:
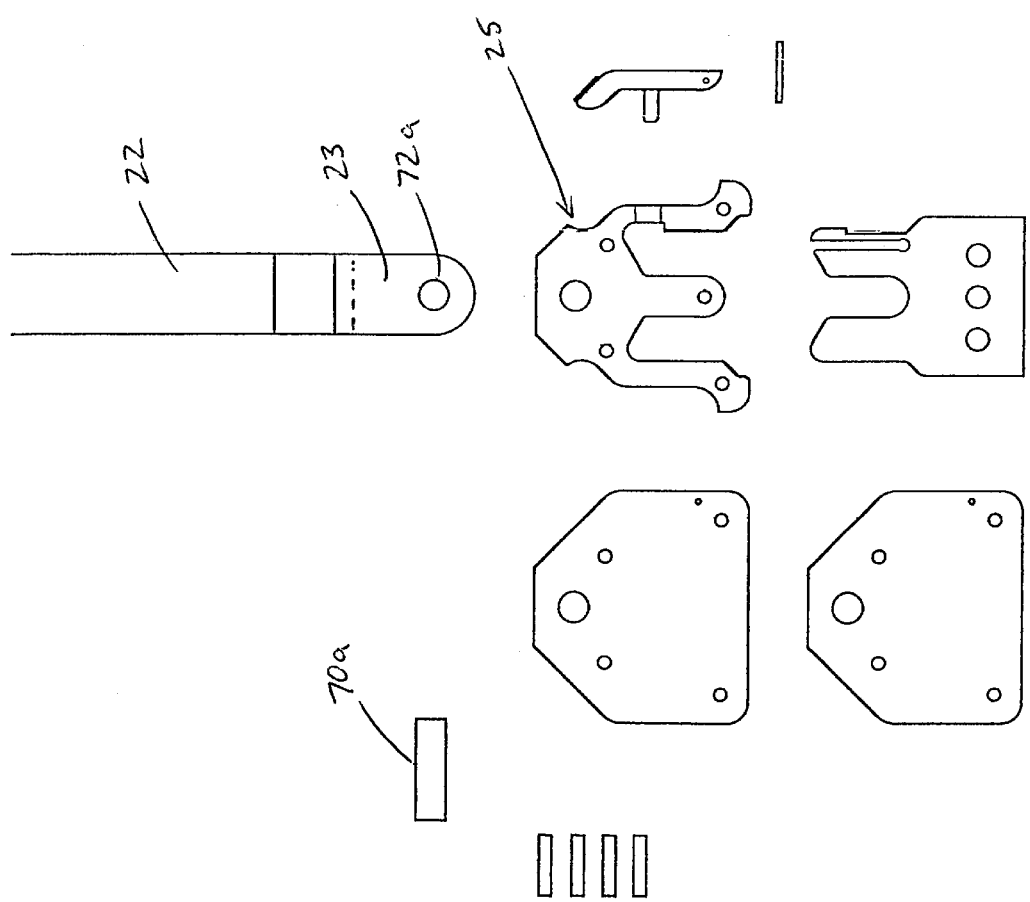
FIG. 20c is an exploded view of the view illustrated in FIG. 19.

FIG. 20a illustrates the pivotal embodiment of FIG. 19 from the side. FIG. 20b is the same illustration as FIG. 20a, but further illustrates connection of the clip 100 to stirrup 2. FIG. 20c illustrate an exploded view of the pivotal embodiment of FIG. 17. As can be seen, upright 22 includes the optional fork member 23, both of which include a clearance hole 72a at the lower end thereof, which are pivotably mounted by a pivot pin 70a around the outsides of the two side plates. Frame 25 also includes a hole for receiving pivot pin 70a. The clip and frame are illustrated as having only one locking member and one release bar, respectively.

Figure 21C:
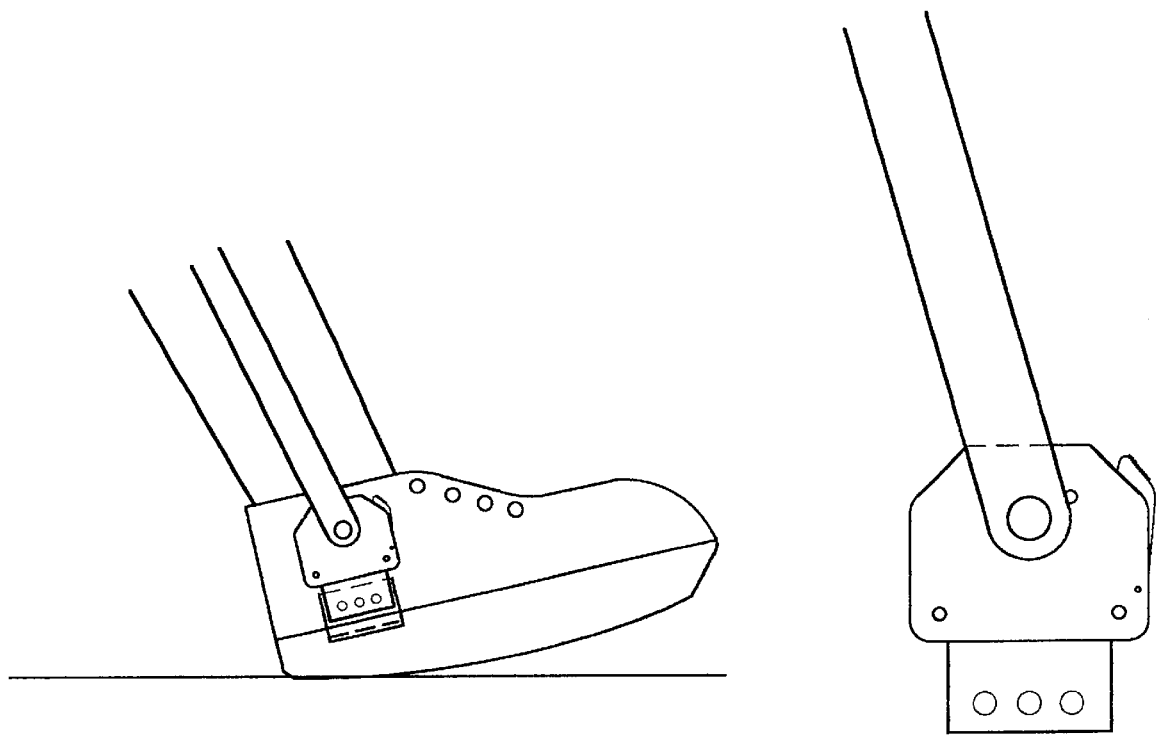
FIG. 21c is a side view of the present invention of FIG. 19 in use in the beginning of a normal striding position.

As illustrated in FIGS. 21a–21c, as the user takes a stride, the upright rotates about the frame assembly, and the clip remains secure in the frame.

The pivotal embodiments use the same components as the standard fixed assembly. The only additional part is the main pivot pin 70. The pivoting or ankle movement occurs at this pin. During the stride, the forces (indicated by arrows in FIGS. 11b–11d) are transferred the same way as the fixed version, however, the frame then transfers the forces to the pivot pin and upright. The forces are then distributed to the rest of the brace.

Options such as toe pickup or limited rotation can be incorporated into this design. Toe pickup is designed to aid the user in pivoting the ankle during the stride. As the user brings the brace forward, the toe pickup option pivots the shoe upward and prevents the toe from dragging on the ground. The toe pickup concept is already used on existing orthopedic braces, and as such is conventional and known in the art. The toe pickup joint requires other screws, springs, linkages, etc. to perform the function, as is known in the art.

Additionally, the upright member can be limited in rotation if necessary. The limited rotation concept is a cross between the fixed clip and the pivotal embodiment. The user might require a joint that pivots or rotates, but not to the full extent of the pivotal clip. This option would utilize the pivotal version and pins would be inserted through the side plates to abut and limit the rotation of the upright.

FIG. 12 illustrates another embodiment of the present invention referred to as the full linear motion ("FLM") joint, which is a quick release, self contained brace ankle joint. The FLM joint is designed to allow the brace and shoe to function as a standard fixed ankle joint, while allowing the upright member 22 to slide vertically and independently of the shoe and clip 100. The FLM joint is designed to eliminate binding at the ankle joint, and creates another degree of freedom for the user. The FLM joint is self contained and functions without the need of supplementary hardware.

The FLM is similar in design to the standard clip. The FLM consists of the frame 22, two side plates 60, 62, five assembly pins 90 and the clip 100 (clip or integral clip stirrup). The FLM uses no release bars or main support pin. The release bars are not needed to retain the clip in this design and the support pin is replaced with the frame tongue 80a. The side plates 60, 62 are fastened to the frame 25a with the assembly pins, which are then peened and ground flush. The design of the FLM frame 25a differs slightly from the standard clip frame, the latching notches for the leaf springs are eliminated and the inner sides of the frame arms 34a and 36a are tapered inward. This taper creates a restrictive mating surface for the spring leafs as the clip slides within the frame. The tapered arms 34a and 36a allow the clip 100 to move within the frame, as required by the brace, yet guide the clip back to the fully inserted position (FIG. 13) when the user's weight is on the shoe/brace (when standing). The frame's sloped areas are unchanged and still provide the wear areas for the clip. The frame tongue guides the clip through the stride and allows and aligns the sliding motion of the clip. The clip 100 is also slightly redesigned to allow the sliding motion within the frame. The tongue slot 136a is designed to slide within the frame tongue and the spring leafs 140a and 142a are tapered at the same angle as the tapered frame arms. As the clip is inserted, the leafs flex and allow the clip to slide into the frame as seen in FIG. 15. During partial insertion, the leafs are deflected inward to create resistive forces between the clip and frame. This prevents the clip from "falling" out of the frame when the brace is not being worn. The force exerted by the leafs also create resistance between the frame arms and clip resulting in a smooth linear motion between the adjacent parts. At the full insertion position (FIG. 13), the leafs are "relaxed" and conform to the inner sides of the frame arms. To insert the shoe/clip into the frame, the user simply aligns the stirrup on each side of the shoe to the lower portion of the frame and pushes until the clip is fully inserted (stops in the frame). The clip is fully inserted at this point, and is retained in the frame by the forces exerted from the spring leafs.

Figure 14A:
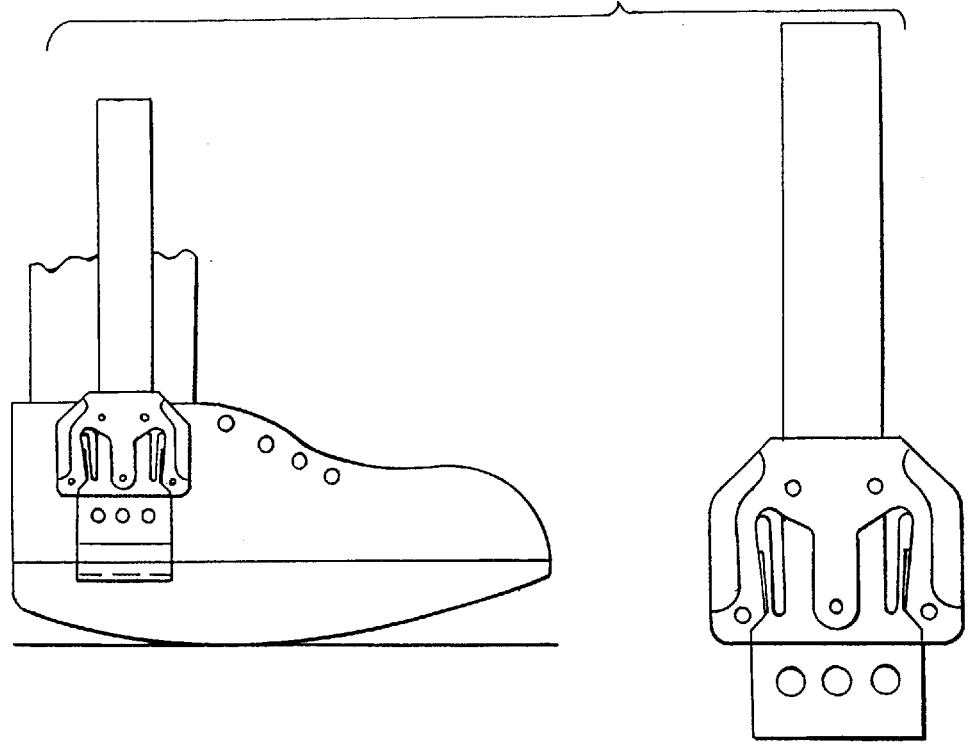
FIG. 14a is a side view of the present invention of FIG. 12 in use in a normal standing position.
Figure 14B:
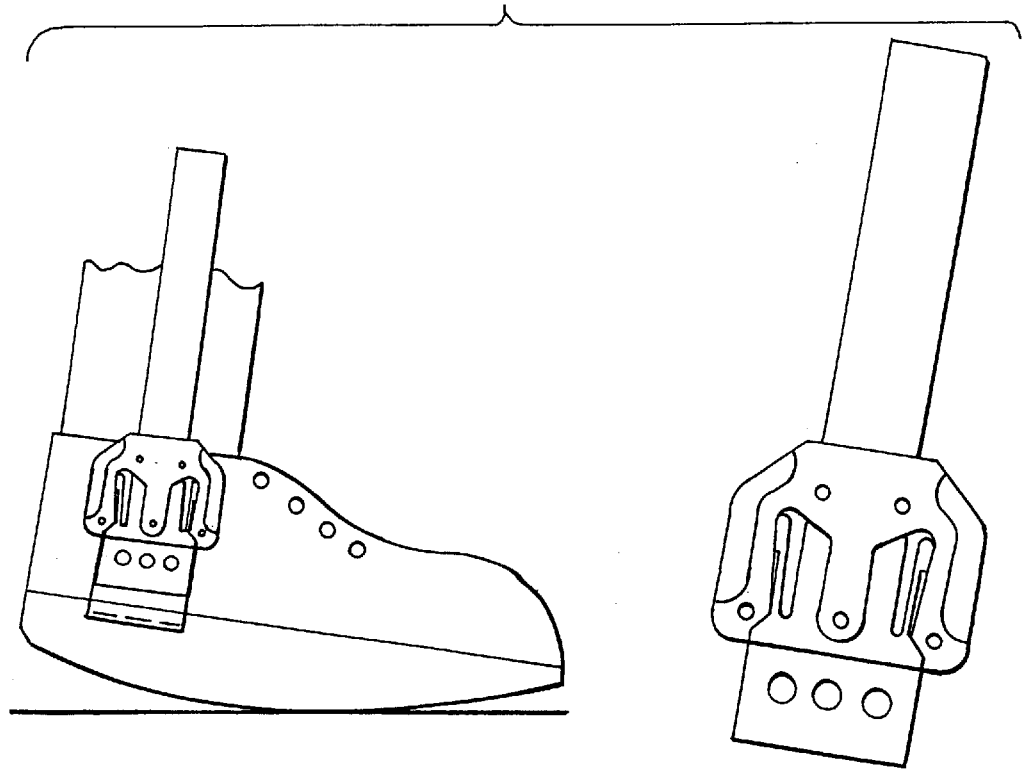
FIG. 14b is a side view of the present invention of FIG. 12 in use in a normal striding position.

As seen in FIG. 14, when the user takes a normal stride, the FLM joint acts as a fixed joint and moves with the shoe and stirrup. However, when the user bends at the knee, as when sitting, the brace is allowed to slide vertically with respect to the shoe/clip as seen in FIG. 15 (similar to a person adjusting or pulling their pants leg while sitting). The vertical movement of the upright may be as much as ½" allowing the brace upright to find its equilibrium position. This vertical movement eliminates binding between the leg and brace, and provides more comfort for the user. The FLM joint can be used where the shoe/brace geometry of the patient makes it difficult to provide a comfortable fit, or where some linear joint motion is needed to create a proper fit.

The clip FLM was designed to be a self contained quick disconnect orthopedic brace ankle joint. The FLM joint can be used on both sides of an orthopedic brace, or only on one side as required to provide the user with a properly fitted and comfortable brace. Although the FLM as described pertains to the fixed ankle joint, the FLM concept will work on the clip pivotal as well.

The operation of the present invention is relatively easy. The clip 100 is inserted into the lower portion of the main frame 25 (between the side plates 60, 62). In order to allow the present invention to function properly, geometry and precision machining are essential. As the clip 100 is initially inserted in the frame assembly 20, the lower sloped areas 46 and 48 of the arms 34 and 36 guide the clip. As the clip is inserted further, the leaf springs 140 and 142 of the clip 100 offer some resistance as they slide toward the locking position. Finally, as the clip 100 is pushed still further, the head portions 144, 146 of leaf springs 140, 142 clear the recessed area 42 and 44 of the main frame 25 and the clip 100 is locked into the frame 25.

Note that there is a small amount of clearance between the sloped portions of the clip 100 and at the main pin 80 location (as seen in FIG. 16). Angles on sloped areas of frame and clip are slightly different to provide surfaces that mate precisely as normal wearing occurs. When new, the angles are slightly different between the clip and frame. The outer portions of the sloped areas mate first. As the parts wear, the surfaces mate precisely. When the clip 100 is fully inserted in the frame 25 (as the user is wearing the brace), the clip notch 136 is forced to rest against the main pin 80. The adjacent sloped surfaces 28, 30, 132 and 134 are also mated at this point, and all exerted forces on the components become compressive forces.

Any forces on the main pin 80 are transferred to the side plates 60, 62 and assembly pins 90. The forces are then distributed throughout the frame assembly 20 and brace. As the user takes a normal stride, the clip 100 forces the frame 25 to rotate or attempt to rotate around the main pin 80. As the clip tries to rotate, the geometry of the clip 100 and frame 25 forces the parts to mate on their adjacent sloped surfaces. Again, the forces are compressive, and are equally distributed over the two sloped areas preventing severe point contact which causes excessive wear.

When the parts are new, the angled surfaces of the frame are at slightly greater angles than the clip's angled surfaces. This angular difference allows the part's adjacent sloped surfaces to mate precisely as normal wearing occurs. Note that the clip's spring latches 140, 142 are designed to not touch the frame catch or recessed area 42, 44 during the stride. The rotation that occurs during the stride is very slight and the spring latches do not travel through enough angular distance to cause interference.

As the clip 100 is inserted in the frame 25, the leaf springs flex approximately three degrees allowing the clip's insertion into the frame 25. As the clip is fully inserted, the leaf springs spring back to their neutral position and the clip is contained securely within the frame housing 25. The spring latches or leaf springs of the clip hold the shoe firmly to the brace when there are no compressive forces (when the user is not standing) on the shoe or brace. As compressive stresses are exerted on the shoe, as during a normal stride, the clip 100 is forced to move through its designed clearances within the frame 25 and transmit the resulting forces to the pins 90 and sloped areas.

This unique design allows the present invention to be a stylish, quick connect/disconnect high quality orthopedic ankle joint without the need of supplementary hardware.

To disengage the clip 100 from the housing 25, the release bars 50, 52 are depressed causing the striking pins 54 and 56 in bores 38, 40 to contact head portions 144 and 146 of leaf springs 140 and 142. The head portions 144, 146 are forced out of recesses 42 and 44 and clip 100 is pulled down and away from the main frame 25. When the clip is installed as a complete set on an orthopedic brace, the above disengaging operation can be performed partially on one side, repeated on the other side, and followed by grasping and pulling the shoe down and away from the brace.

Many types of braces exist for different applications, but the present invention is preferably a steel or aluminum orthopedic leg brace. Further, while the present invention could be used for non-specific braces, preferably, and as illustrated, the present invention is an ankle joint.

It is to be understood that the embodiments herein described are merely illustrative of the principles of the present invention. Various modifications may be made by those skilled in the art without departing from the spirit or scope of the claims which follow.

What is claimed is:

1. A quick release mechanism for an orthopedic support member, comprising:
    a clip;
    a clip housing for selectively and removably receiving said clip;
    means for preventing relative movement between said clip and said clip housing when said clip is received in said clip housing;
    at least one means for locking said clip to said clip housing located on one of said clip and said clip housing, wherein said means for locking is distinct from said means for preventing relative movement; and
    a means for pivotally associating one of said clip and said clip housing with said orthopedic support member.

2. The quick release mechanism of claim 1, wherein said means for preventing relative movement between said clip and said clip housing includes a main support pin disposed between said clip and said clip housing.

3. The quick release mechanism of claim 2, wherein said clip includes a tongue including a notch for receiving said main support pin, and said clip housing having a middle section including a notch for receiving said main support pin.

4. The quick release mechanism of claim 3, wherein said notch of said tongue and said notch of said middle section receive said main support pin when said clip is received in said clip housing.

5. The quick release mechanism of claim 4, wherein said tongue includes sloping end surfaces, and said middle section includes sloping edge surfaces, said sloping end surfaces of said tongue and said sloping edge surfaces of said middle section mating clip is received in said clip housing.

6. The quick release mechanism of claim 3, wherein said main support pin is integral with said clip tongue.

7. The quick release mechanism of claim 2, wherein said means for preventing relative movement between said clip and said clip housing further includes a pair of side plates mounted to said clip housing.

8. The quick release mechanism of claim 7 further comprising at least one means for facilitating removal of said clip from said clip housing located on one of said clip or said clip housing.

9. The quick release mechanism of claim 1, wherein said at least one means for locking facilitates said clip selectively locking into said clip housing to form a rigid connection between said clip and said clip housing, wherein forces are distributed through said rigid connection into said orthopedic support member to prevent rotation between said clip and said clip housing.

10. The quick release mechanism of claim 9, wherein said clip comprises a clip tongue having sloping end surfaces and said clip housing comprises a middle section having sloping edge surfaces for mating with the sloping end surfaces of said clip tongue when said clip is received in said clip housing.

11. The quick release mechanism of claim 9, wherein said clip comprises a middle section having sloping edge surfaces and said clip housing comprises a clip housing tongue having sloping end surfaces for mating with the sloping edge surfaces of said clip when said clip is received in said clip housing.

12. The quick release mechanism of claim 9, wherein said selective locking is provided by a friction fit between said clip and said clip housing when said clip is received in said clip housing.

13. The quick release mechanism of claim 9, wherein said selective locking is released by a release means for releasing said clip from said clip housing when said clip is selectively locked into said clip housing.

14. A quick release orthopedic brace ankle joint connecting an upright brace member to a shoe stirrup, comprising:
    a clip housing pivotally connected at an end of said upright brace member, said clip housing including
        a clip housing having a middle section, a first arm extending from said middle section, and a second arm opposite said first arm and extending from said middle section, said first arm, second arm, and middle section of said clip housing defining a C-shaped opening,
        at least one release bar pivotably mounted proximate one of said first arm and said second arm, respectively, said at least one release bar having a striking pin extending therefrom, said one of said first arm and said second arm of said clip housing having a bore for receiving therethrough said striking pin,
    two side plates, one each mounted on opposite sides of said clip housing, and
    a main support pin, said main support pin mounted between said side plates and in said C-shaped opening of said clip housing;
    a clip member at an end of said shoe stirrup, said clip member including
    a main portion connected to said end of said shoe stirrup, and
    a tongue portion extending from said main portion, said tongue portion removably insertable into said C-shaped opening of said clip housing, said tongue portion having
        a central flange, and at least one locking member extending from said main portion on a side of said central flange, said at least one locking member and said central flange defining a slot therebetween, said at least one locking member cooperating with said one of said first and said second arm of said clip housing to selectively and releasably fasten said stirrup to said upright brace member.

15. The quick release orthopedic brace ankle joint of claim 14, wherein said at least one locking member having an enlarged head portion, said one of said first and said second arm of said clip housing having a recessed portion near said bore, said recessed portion of said one of said first and said second arm receiving said head portion to lock said clip member in said clip housing upon insertion of said tongue portion into said C-shaped opening.

16. The quick release orthopedic brace ankle joint of claim 15, wherein said middle section of said clip housing has sloped edges which slope into said C-shaped opening, and a notch for receiving said main support pin, said central flange of said tongue portion having sloped edges and a notch for receiving said main support pin, said sloped edges of said central flange mating with said sloped edges of said middle section when said clip member is locked in said clip housing.

17. The quick release orthopedic brace ankle joint of claim 16, wherein said first arm and said second arm of said clip housing has sloped edges at an end thereof, and said main portion of said clip member having sloped edges, said sloped edges of said first and said second arms mating with said sloped edges of said main portion when said clip member is locked in said clip housing.

18. The quick release orthopedic brace ankle joint of claim 15, wherein said clip member locks into said clip housing to form a rigid connection between said clip member and said clip housing, wherein forces in said ankle joint of said orthopedic brace are distributed through said main support pin and side plates and into said upright member and said shoe stirrup to prevent rotation between said clip member and said clip housing.

19. The quick release orthopedic brace ankle joint of claim 15, wherein said at least one release bar is selectively pivotable toward said main support pin whereupon said striking pin engage said head portion to disengage said head portion from said recessed portion to release said clip member from said clip housing.

20. The quick release orthopedic brace ankle joint of claim wherein said side plates include beveled upper corners to allow said first and said second release bars to pivot toward said main support pin.

21. A quick release orthopedic brace having an upright member and a shoe stirrup, comprising:
  a clip member;
  a clip housing for selectively and removably receiving said clip member;
  a means for preventing relative movement between said clip member and said clip housing when said clip member is received in said clip housing;
  a means for pivotally associating one of said clip member and said clip housing with said upright member;
  a means for associating one of said clip member and said clip housing with said shoe stirrup; and
  a means for selectively locking said clip member into said clip housing to form a rigid connection between said clip member and said clip housing;
  wherein forces are distributed through said rigid connection into said shoe stirrup without said forces being substantially imposed on said means for selectively locking.

22. The quick release orthopedic brace of claim 21 wherein said means for selectively locking comprise mechanical locking means.

23. The quick release orthopedic brace of claim 22 further comprising a means for releasing said mechanical locking means.

24. The quick release orthopedic brace of claim 21, wherein said clip member comprises a tongue having sloping end surfaces and said clip housing comprises a middle section having sloping edge surfaces for mating with the sloping end surfaces of said clip member tongue when said clip member is received in said clip housing.

25. The quick release orthopedic brace of claim 21, wherein said clip member comprises a middle section having sloping edge surfaces and said clip housing comprises a tongue having sloping end surfaces for mating with the sloping end surfaces of said clip member tongue when said clip member is received in said clip housing.

26. The quick release orthopedic brace of claim 21, wherein said clip member comprises a tongue including a notch and said clip housing having a middle section including a notch.

27. The quick release orthopedic brace of claim 26, wherein said means for preventing relative movement between said clip member and said clip housing includes a main support pin selectively disposed within at least one of said notch of said clip member tongue and said notch of said middle section when said clip member is received in said clip frame.

28. The quick release orthopedic brace of claim 27, wherein said main support pin is integral with said clip member tongue.

29. The quick release orthopedic brace of claim 21, wherein said means for preventing relative movement between said clip member and said clip housing includes a pair of side plates mounted to said clip housing.

30. The quick release orthopedic brace of claim 21 further comprising a means for releasing said clip member from said clip housing.

31. The quick release orthopedic brace of claim 21, wherein said selective locking is provided by a friction fit between said clip member and said clip housing when said clip is received in said clip housing.

32. The quick release orthopedic brace of claim 21, wherein said selective locking is released by a release means for releasing said clip member from said clip housing when said clip member is selectively locked into said clip housing.

33. The quick release orthopedic brace of claim 21, wherein one of said clip member and said clip housing is adapted to be integral with said shoe stirrup and the other of said clip member and said clip housing is adapted to be pivotally associated with said upright member via said means for pivotally associating.

34. A quick release mechanism for an orthopedic support member comprising: an upright member;
  a clip;
  a clip housing for selectively and removably receiving said clip, said upright member pivotally associated with one of said clip and said clip housing via a means for associating one of said clip and said clip housing with said orthopedic support member and allowing for pivotal movement of said upright member;
  means for preventing relative movement between said clip and said clip housing when said clip is received in said clip housing;
    wherein said means for preventing relative movement between said clip and said clip housing includes a main support pin disposed between said clip and said clip housing; and wherein said clip includes a tongue including a notch for receiving said main support pin, and said clip housing having a middle section including a notch for receiving said main support pin.

35. The quick release mechanism of claim 34, wherein said notch of said tongue and said notch of said middle section receive said main support pin when said clip is received in said clip housing.

36. The quick release mechanism of claim 34, wherein a main support pin is integral with said clip tongue.

37. The quick release mechanism of claim 34, wherein said tongue includes sloping end surfaces, and said middle section includes sloping edge surfaces, said sloping end surfaces of said tongue and said sloping edge surfaces of said middle section mating when said clip is received in said clip housing.

38. A quick release orthopedic brace having an upright member and a shoe stirrup, comprising:
   a clip member;
   a clip housing for selectively and removably receiving said clip member;
   a means for preventing relative movement between said clip member and said clip housing when said clip member is received in said clip housing;
   a means for pivotally associating one of said clip member and said clip housing with said upright member; and
   a means for associating one of said clip member and said clip housing with said shoe stirrup;
      wherein said clip member selectively locks into said clip housing to form a rigid connection between said clip member and said clip housing;
      wherein forces are distributed through said rigid connection into said shoe stirrup;
   wherein said clip member comprises a tongue including a notch and said clip housing having a middle section including a notch; and
   wherein said means for preventing relative movement between said clip member and said clip housing includes a main support pin selectively disposed within at least one of said notch of said clip member tongue and said notch of said middle section when said clip member is received in said clip housing.

39. The quick release orthopedic brace of claim 37, wherein said main support pin is integral with said clip member tongue.

40. A quick release mechanism for an orthopedic support member, comprising:
   a clip;
   a clip housing for selectively and removably receiving said clip;
   means for preventing relative movement between said clip and said clip housing when said clip is received in said clip housing, wherein said means for preventing relative movement comprises a main support pin disposed between said clip and said clip housing and a distinct means for locking said clip to said clip housing; and
   a means for associating one of said clip and said clip housing with said orthopedic support member and allowing for pivotal movement therein.

\* \* \* \* \*